United States Patent
Fujii et al.

(10) Patent No.: US 10,200,637 B2
(45) Date of Patent: Feb. 5, 2019

(54) IMAGE PICKUP APPARATUS INCLUDING LIGHT SOURCE, IMAGE SENSOR, AND CONTROL CIRCUIT

(71) Applicant: Panasonic Intellectual Property Management Co., Ltd., Osaka (JP)

(72) Inventors: Toshiya Fujii, Shiga (JP); Takamasa Ando, Osaka (JP); Tatsuya Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 16 days.

(21) Appl. No.: 15/459,021

(22) Filed: Mar. 15, 2017

(65) Prior Publication Data

US 2017/0289468 A1 Oct. 5, 2017

(30) Foreign Application Priority Data

Mar. 31, 2016 (JP) .................. 2016-072346

(51) Int. Cl.
*H04N 5/225* (2006.01)
*H04N 9/04* (2006.01)
(Continued)

(52) U.S. Cl.
CPC .......... *H04N 5/353* (2013.01); *A61B 5/0062* (2013.01); *A61B 5/0261* (2013.01);
(Continued)

(58) Field of Classification Search
CPC ... H04N 5/2256; H04N 5/3745; A61B 5/0033
(Continued)

(56) References Cited

U.S. PATENT DOCUMENTS

| | | | |
|---|---|---|---|
| 2010/0201797 A1* | 8/2010 | Shizukuishi | A61B 1/045 348/68 |
| 2013/0148326 A1* | 6/2013 | Goldfain | G01J 3/0224 362/19 |

(Continued)

FOREIGN PATENT DOCUMENTS

| | | |
|---|---|---|
| JP | 6-261107 | 10/1993 |
| JP | 2002-165230 | 6/2002 |

(Continued)

OTHER PUBLICATIONS

Takamasa Ando et al., U.S. Appl. No. 15/175,340, filed Jun. 7, 2016, entitled "Imaging Apparatus Including Light Source That Emits Pulsed Light, Image Sensor, and Control Circuit".

(Continued)

*Primary Examiner* — Anthony J Daniels
(74) *Attorney, Agent, or Firm* — McDermott Will & Emery LLP

(57) ABSTRACT

An image pickup apparatus includes: a first light source which, in operation, emits first pulsed light to project a first image of a first pattern at a first position in a predetermined region of a subject, and emits second pulsed light to project a second image of a second pattern at a second position, different from the first position, in the predetermined region of the subject; an image sensor including multiple pixels each including a photodetector that, in operation, converts received light into a signal charge, and a first accumulator and a second accumulator each of which, in operation, accumulates the signal charge; and a control circuit which, in operation, controls the first light source and the image sensor.

13 Claims, 24 Drawing Sheets

(51) Int. Cl.
*H04N 5/353* (2011.01)
*H04N 5/378* (2011.01)
*H04N 5/235* (2006.01)
*A61B 5/00* (2006.01)
*A61B 5/026* (2006.01)

(52) U.S. Cl.
CPC ......... *A61B 5/4064* (2013.01); *H04N 5/2353* (2013.01); *H04N 5/378* (2013.01)

(58) Field of Classification Search
USPC .................................................. 348/207.99
See application file for complete search history.

(56) References Cited

U.S. PATENT DOCUMENTS

| | | | |
|---|---|---|---|
| 2014/0086016 A1 | 3/2014 | Wada | |
| 2018/0070830 A1* | 3/2018 | Sutin | A61B 5/0075 |
| 2018/0077367 A1* | 3/2018 | Feder | H04N 5/265 |

FOREIGN PATENT DOCUMENTS

| | | | | |
|---|---|---|---|---|
| JP | 2012-125370 | 7/2012 | | |
| JP | 2012-165809 | 9/2012 | | |
| JP | 2012-230005 | 11/2012 | | |
| JP | 2015-010988 | 1/2015 | | |
| WO | WO-2017099395 A1 * | 6/2017 | ........... | A61B 5/0075 |

OTHER PUBLICATIONS

Takamasa Ando et al., U.S. Appl. No. 15/176,165, filed Jun. 8, 2016, entitled "Imaging Apparatus Including Light Source That Emits Pulsed Light, Image Sensor, and Control Circuit".

* cited by examiner

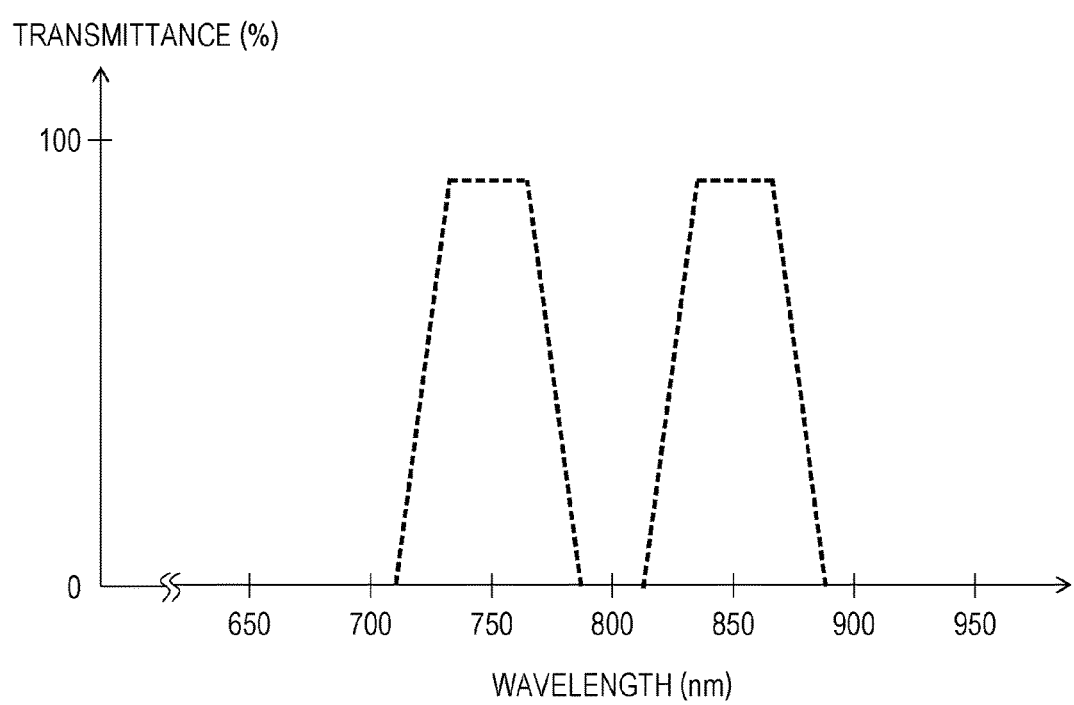

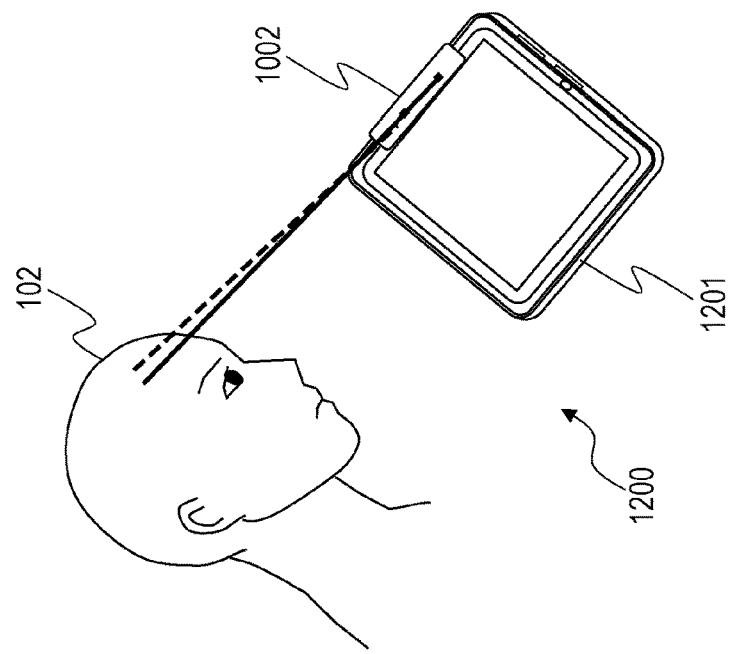
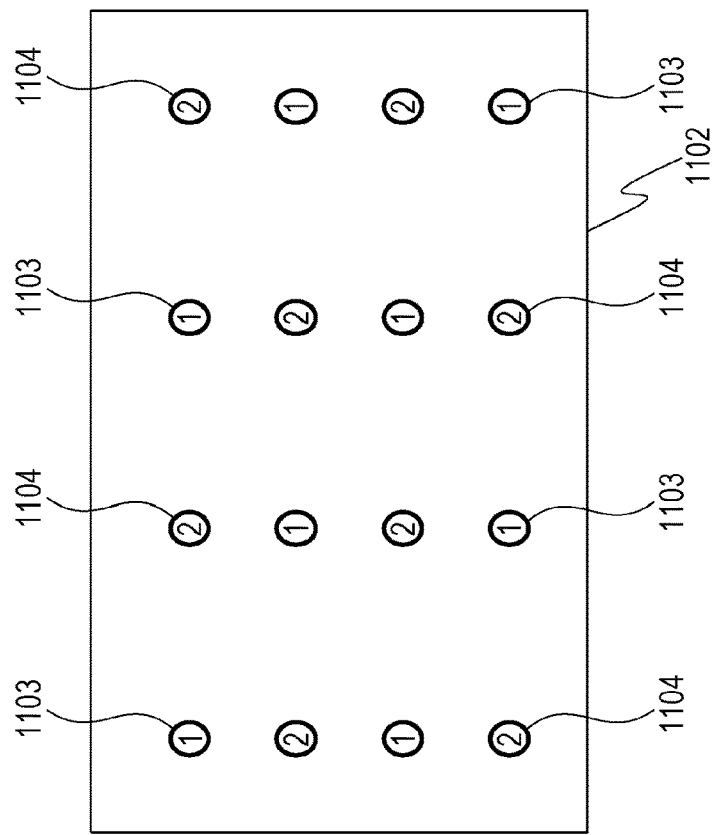

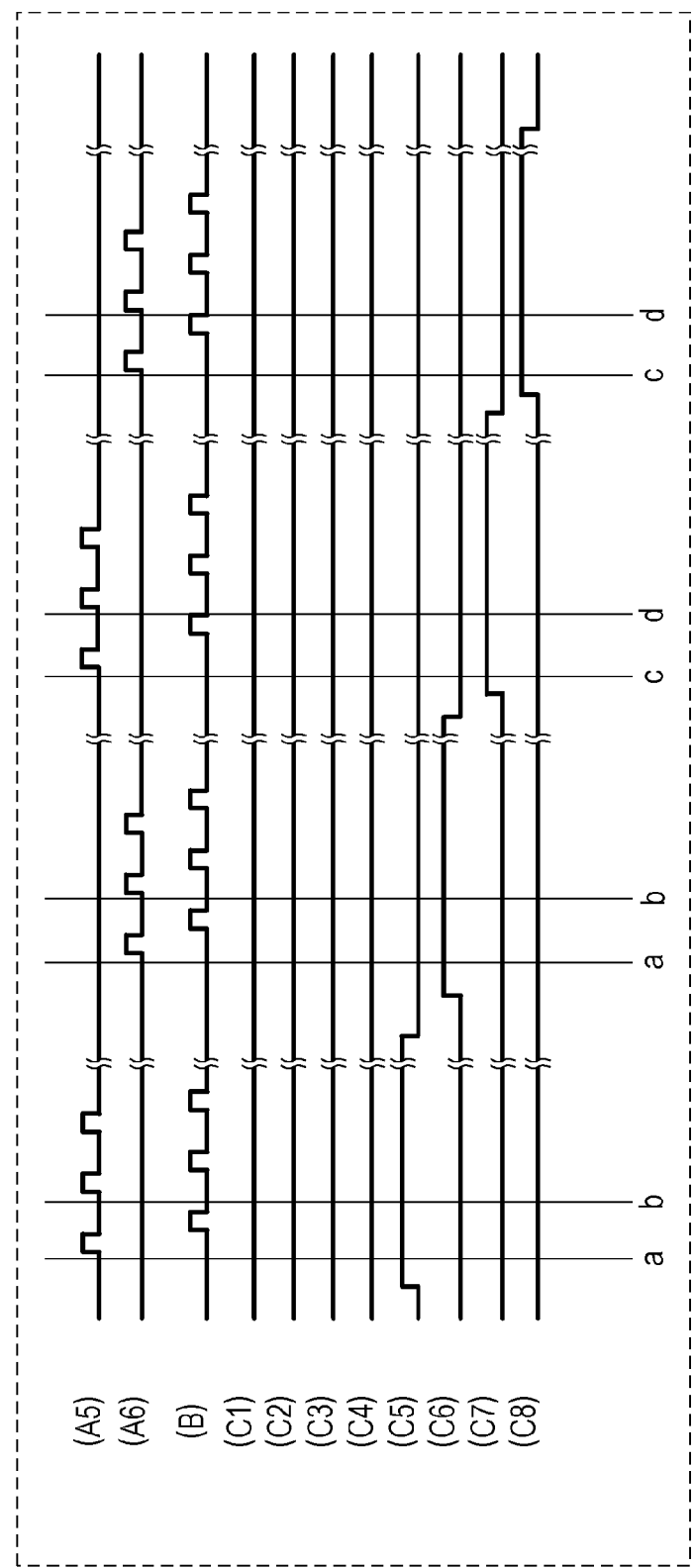

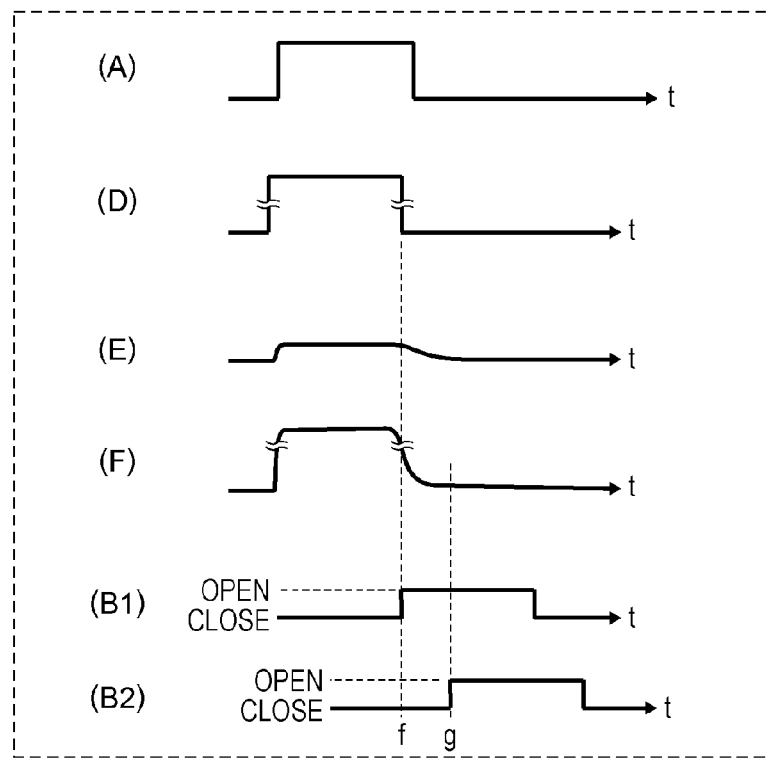
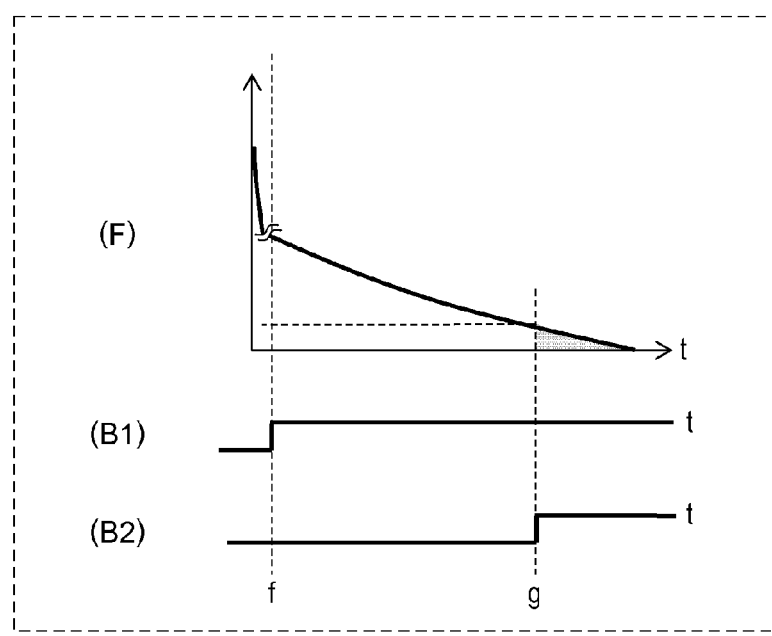

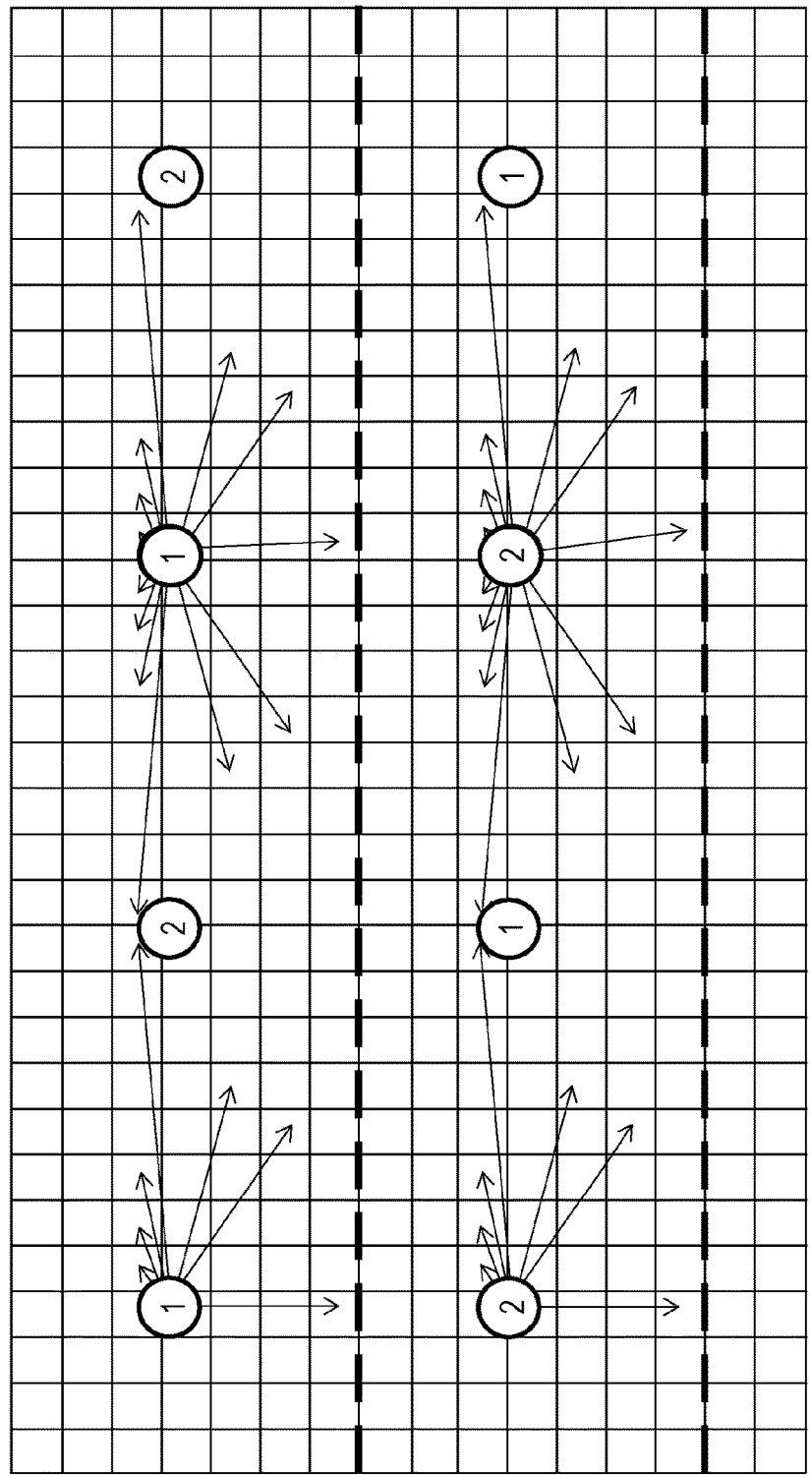

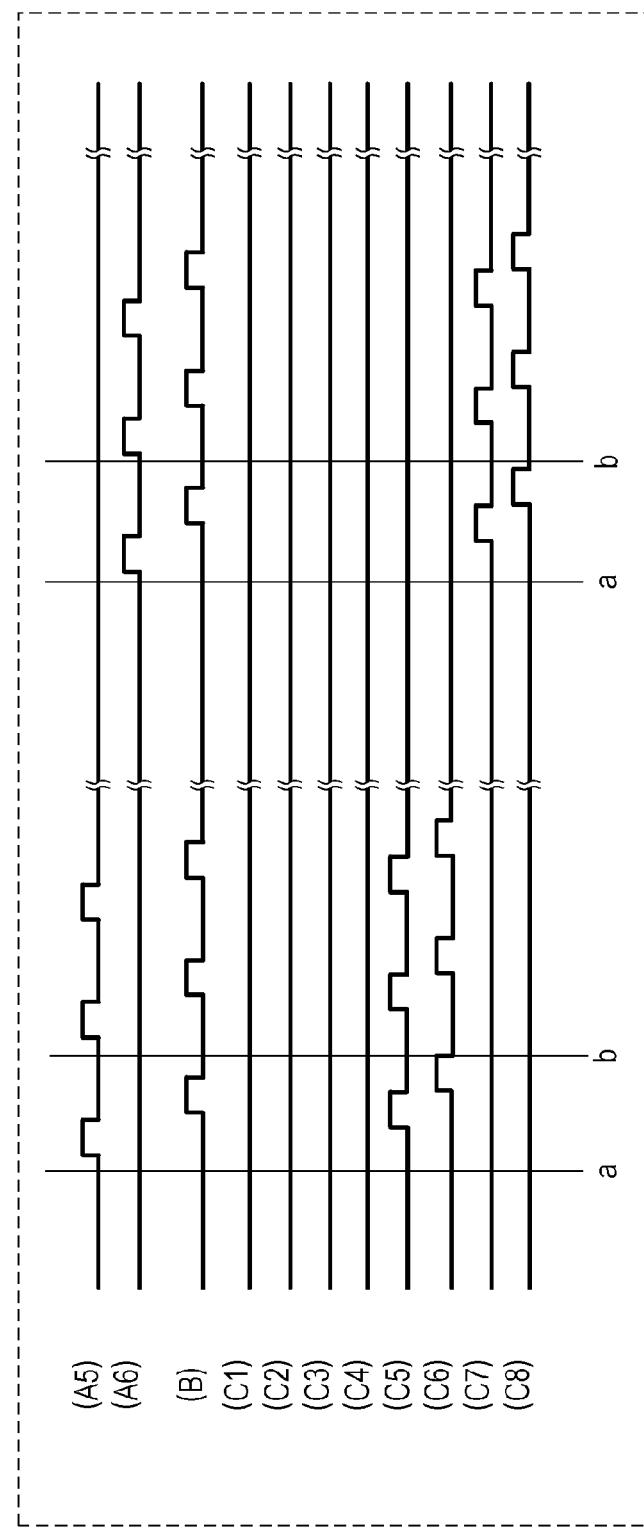

IMAGE PICKUP APPARATUS INCLUDING LIGHT SOURCE, IMAGE SENSOR, AND CONTROL CIRCUIT

BACKGROUND

1. Technical Field

The present disclosure relates to a technique to acquire internal information on a measurement object in a contactless manner. For example, the present disclosure relates to a technique to separate an image based on light reflected from and around a surface of a light-scattering body to be measured from an image based on light which reaches the inside of the light-scattering body and then returns to the surface thereof.

2. Description of the Related Art

A method of irradiating an object with light and acquiring internal information on the object by use of information of the light received through the object is used in the fields of bioinstrumentation and material analysis. In this method, reflected components from the surface of the object may cause noise and thus pose a problem. In the field of bioinstrumentation, for example, a method described in Japanese Unexamined Patent Application Publication No. 2012-125370 (JP 2012-125370 A) is known as a method of acquiring only desired internal information by removing noise attributed to reflected components from a surface. According to JP 2012-125370 A, a controller changes either an irradiation point or a detection point as needed with a light source or an optical detector positioned in a contactless manner. Thus, the optical detector can detect multiple signals attributed to light having passed through different paths inside a subject, while an analyzer can select a certain signal out of the multiple signals obtained with the optical detector and calculate a light absorption characteristic in the subject by using the selected signal.

Meanwhile, Japanese Unexamined Patent Application Publication No. 2012-230005 (JP 2012-230005 A) discloses a defect inspection apparatus which includes means for applying irradiation light in bright and dark patterns while switching the illumination patterns and modulating the irradiation luminance within one exposure period, and a processor to detect a defect on a surface to be inspected.

SUMMARY

In one general aspect, the techniques disclosed herein feature an image pickup apparatus including: a first light source which, in operation, emits a first pulsed light beam to project a first image of a first pattern at a first position in a predetermined region of a subject, and emits a second pulsed light beam to project a second image of a second pattern at a second position in the predetermined region of the subject, the second position being different from the first position; an image sensor including pixels, each pixel including a photodetector which, in operation, converts received light into a signal charge, and a first accumulator and a second accumulator each of which, in operation, accumulates the signal charge at a different timing; and a control circuit which, in operation, controls the first light source and the image sensor. The control circuit, in operation, causes the first light source to emit the first pulsed light beam, causes the first accumulator to accumulate a first signal charge generated in the photodetector by a first return light corresponding to the first pulsed light beam, causes the first light source to emit the second pulsed light beam at a different time point from a time point of the emission of the first pulsed light beam, and causes the second accumulator to accumulate a second signal charge generated in the photodetector by a second return light corresponding to the second pulsed light beam.

It should be noted that general or specific aspects described above may be implemented as a system, a method, a computer program, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a graph depicting spectral transmittance of an optical double band pass filter, which is designed to pass light components with wavelengths of 750 nm and 850 nm while shielding light components having other wavelengths;

FIG. 13A is a diagram showing a usage scene of the image pickup apparatus of the Embodiment 2;

FIG. 13B is a diagram showing an example of a light irradiation pattern to be emitted to the head (the forehead);

FIG. 14B is another timing chart showing the operations of the image pickup apparatus of the Embodiment 2;

FIG. 15A is a timing chart showing detailed operations of the image pickup apparatus of the Embodiment 2;

FIG. 15B is another timing chart showing detailed operations of the image pickup apparatus of the Embodiment 2;

FIG. 16 is a diagram showing relations between a dot irradiation pattern and pixel positions on the time-resolved image sensor in the Embodiment 2;

FIG. 17B is another timing chart showing the operations of the image pickup apparatus of the Embodiment 3;

DETAILED DESCRIPTION

Figure 1:
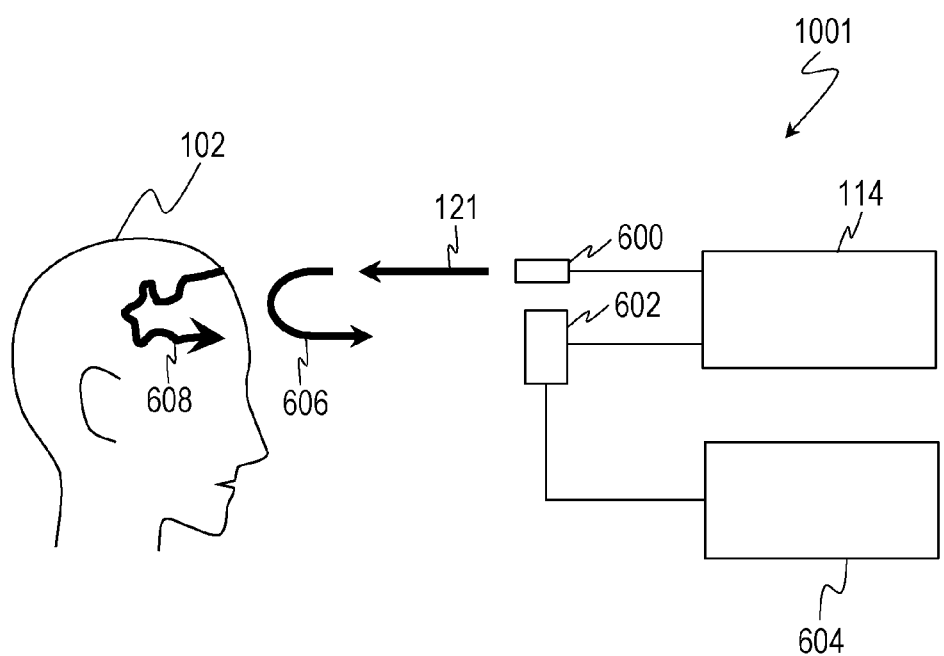
FIG. 1 is a diagram showing a configuration of an image pickup apparatus.

The earnest studies conducted by the inventors of the present disclosure have revealed that the above-described techniques according to JP 2012-125370 A and JP 2012-230005 A have limitations in achieving higher accuracy, higher density, and higher speed.

Prior to the description of an Embodiment of the present disclosure, a method described in JP 2012-125370 A will be discussed below as the related art to observe internal information on an object while separating a shallow part from a deep part.

JP 2012-125370 A discloses a technique for an optical bioinstrumentation apparatus using visible light or near infrared light to separate and remove an adverse effect of surface layer components such as skin blood flow components mixed with signal components. JP 2012-125370 A mainly has three objectives. The first objective is to eliminate an adverse effect of components contained in signals and originating from tissues other than the brain, which include local blood flows, thereby separating and extracting only the signals originating from the brain or the cerebral cortex. The second objective is to separate and extract components originating from the brain and components originating from the skin as well as components contained in both the brain and the skin in common in a more versatile manner. The third objective is to separate a signal originating from the brain from a signal originating from the skin while taking into account an individual difference in contribution rates of these two signals.

In order to separate the signal originating from the brain from the signal originating from the skin, according to JP 2012-125370 A, light transmitters and light receivers are arranged so as to achieve measurements using multiple light transmitter—light receiver distances and to cause the light to propagate through the gray matter and the scalp and then be received by each light receiver. A measurement is conducted while switching on and off states or the strength of each light source power, or switching on and off states, the gain strength, and the like of each detector as needed, so as to fulfill the measurement in which signal detection can be performed without having mutual interference of the signals from the multiple light sources and each light receiver can receive the light at an appropriate strength level. Furthermore, in an analysis, a signal separation method such as an independent component analysis is conducted by using data obtained at respective measurement points. Then, one or more separation components thus obtained are each subjected to determination as to whether or not the separation component is a signal component originating from the brain or a signal component originating from the skin by using a dependency of a weighted value at each measurement point on the light transmitter—light receiver distance. Thereafter, a measurement signal regarding each of the light transmitter—light receiver distances is reconstructed by using only one or more separation components to be used.

A controller changes an irradiation point or a detection point as appropriate, thereby causing an optical detector to detect the multiple signals of the light having passed through different paths in a subject. An analyzer selects a certain signal out of the multiple signals obtained with the optical detector and calculates a light absorption characteristic in the subject by using the selected signal.

The investigation conducted by the inventors of the present disclosure has revealed that the method described in JP 2012-125370 A requires the measurement to be performed while appropriately changing the position of the irradiation point or of the detection point, and allows detection of only a single piece of data between a certain one of the light transmitters and the corresponding light receiver at a time. Therefore, the method has a problem of a difficulty in satisfying both high speed and high resolution at the same time.

On the other hand, JP 2012-230005 A describes a method in which illumination patterns are switched within one exposure period. However, according to this method, each pixel in an image sensor is configured to detect a value of integral of changed patterns in illumination light. Hence, arithmetic processing across multiple frames is required in order to perform computation of a deep part and a shallow part of a subject.

The inventors of the present disclosure have realized an image pickup apparatus which performs light application to multiple positions on a surface of a subject and utilizes time-resolved image sensor outputs at multiple points. This image pickup apparatus can image distribution of biological components both at a shallow part and at a deep part of a subject at high accuracy, high density, and high speed by executing arithmetic processing within one frame.

An outline of an aspect of the present disclosure is as follows.

An image pickup apparatus according to the aspect of the present disclosure includes a first light source which, in operation, emits a first pulsed light beam to project a first image of a first pattern at a first position in a predetermined region of a subject, and emits a second pulsed light beam to project a second image of a second pattern at a second position in the predetermined region of the subject, the second position being different from the first position, an image sensor including pixels, each pixel including a photodetector which, in operation, converts received light into a signal charge, and a first accumulator and a second accumulator each of which, in operation, accumulates the signal charge at a different timing, and a control circuit which, in operation, controls the first light source and the image sensor. The control circuit, in operation, causes the first light source to emit the first pulsed light beam, causes the first accumulator to accumulate a first signal charge generated in the photodetector by a first return light corresponding to the first pulsed light beam, causes the first light source to emit the second pulsed light beam at a different time point from a time point of the emission of the first pulsed light beam, and causes the second accumulator to accumulate a second signal charge generated in the photodetector by a second return light corresponding to the second pulsed light beam.

The image pickup apparatus may further include a signal processing circuit which, in operation, generates image information by using the first signal charge and the second signal charge.

Each of the first pattern and the second pattern is a pattern including dots, for example.

Each of the first pattern and the second pattern is a pattern including rings, for example.

Each of the first pattern and the second pattern is a pattern including lines, for example.

In operation, the control circuit may cause the first light source to emit a plurality of first pulsed light beams, each of the plurality of first pulsed light beams being the first pulsed light beam, and the control circuit may cause the first light source to emit a plurality of second pulsed light beams, each of the plurality of second pulsed light beams being the second pulsed light beam.

The image pickup apparatus may further include a second light source which, in operation, emits a third pulsed light beam to project a third image of a third pattern at a third position in the predetermined region of the subject, the third position being different from the first and second positions, and emits a fourth pulsed light beam to project a fourth image of a fourth pattern at a fourth position in the predetermined region of the subject, the fourth position being different from the first, second, and third positions. Each of the pixels in the image sensor may include a third accumulator and a fourth accumulator each of which, in operation, accumulates the signal charge. The first light source may, in operation, emit the light beam in a first wavelength range, and the second light source may, in operation, emit the light beam in a second wavelength range different from the first wavelength range. The control circuit may, in operation, further control the second light source, cause the second light source to emit the third pulsed light beam, cause the third accumulator to accumulate a third signal charge generated in the photodetector by a third return light corresponding to the third pulsed light beam, cause the second light source to emit the fourth pulsed light beam at a different time point from a time point of the emission of the third pulsed light beam, and cause the fourth accumulator to accumulate a fourth signal charge generated in the photodetector by a fourth return light corresponding to the fourth pulsed light beam.

The signal processing circuit may, in operation, generate the image information by using the first to fourth signal charges.

In the image pickup apparatus, the subject may be a light-scattering body, the first signal charge may be an internally scattered light component originating from the first pulsed light beam and arriving from the subject, and the second signal charge may be an internally scattered light component originating from the second pulsed light beam and arriving from the subject.

In the image pickup apparatus, each of the plurality of pixels in the image sensor may further include a third accumulator and a fourth accumulator each of which, in operation, accumulates the signal charge, and the control circuit may, in operation, causes the first light source to emit the first pulsed light beam at a first time point and at a second time point, cause the first accumulator to accumulate the first signal charge after a lapse of a first time period from the first time point, cause the third accumulator to accumulate the first signal charge after a lapse of a second time period from the second time point, the second time period being longer than the first time period, cause the first light source to emit the second pulsed light beam at a third time point and at a fourth time point, cause the second accumulator to accumulate the second signal charge after a lapse of a third time period from the third time point, and cause the fourth accumulator to accumulate the second signal charge after a lapse of a fourth time period from the fourth time point, the fourth time period being longer than the third time period.

An image pickup apparatus according to another aspect of the present disclosure may include a light source which, in operation, emits a first pulsed light beam to project an image of a prescribed pattern in a predetermined region of a subject, an image sensor including pixels, each pixel including a photodetector which converts received light into a signal charge, and a first accumulator and a second accumulator each of which, in operation, accumulates the signal charge, and a control circuit which, in operation, controls the light source and the image sensor. The control circuit may, in operation, cause the light source to emit the first pulsed light beam at a first time point, cause the first accumulator to accumulate the signal charge in a period after the first time point until the second time point, and cause the second accumulator to accumulate the signal charges after the second time point.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or a large scale integration (LSI). The LSI or IC can be integrated into one chip, or also can be a combination of plural chips. For example, functional blocks other than a memory may be integrated into one chip. The name used here is LSI or IC, but it may also be called system LSI, very large scale integration (VLSI), or ultra large scale integration (ULSI) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

An embodiment of an image pickup apparatus according to the present disclosure will be described below with reference to the accompanying drawings.

Before explaining Embodiments of the image pickup apparatus, an outline of operations of the image pickup apparatus will be described.

FIG. 1 shows a configuration of an image pickup apparatus 1001. The image pickup apparatus 1001 includes: a control circuit 114; a light source 600 and an image sensor 602 which are controlled by the control circuit 114; and a signal processing circuit 604 which processes outputted signals from the image sensor 602. Here, the light source 600 does not always have to be built in the image pickup apparatus 1001. The light source 600 may be provided outside the image pickup apparatus 1001 in so far as the control circuit 114 can control the light source 600. Note that the same applies to other examples in this specification.

Light emitted from the light source 600 is reflected from a head 102 including a forehead of a subject, and is made incident on the image sensor 602. The image sensor 602 converts the incident light into an electric signal and outputs the electric signal. The control circuit 114 adjusts an irradiation position and power of the light from the light source 600 based on the signal outputted from the image sensor 602.

The control circuit 114 conducts two initial operations, namely, a measurement operation of a distance to the head 102, and an irradiation adjustment operation.

First, the distance measurement operation to be conducted by the control circuit 114 will be described. The control circuit 114 specifies a position of the head 102 and a distance to the head 102 based on the electric signal (such as a signal representing an image) outputted from the image sensor 602 during the light emission from the light source 600. For example, the control circuit 114 can measure the distance to the head 102 by using the TOF (time-of-flight) technique. The TOF technique is used to measure time required for illumination light (such as pulsed light) to be reflected from the head 102 and to reach the image sensor 602, i.e., the time of flight. The control circuit 114 can detect the distance to the head 102 based on the time from a point of emission of the pulsed light from the light source 600 to a point of detection of the pulsed light by the image sensor 602. The time of flight can be measured on the basis of a difference between a phase of light to be detected with each detection element of the image sensor 602 and a phase of light at the light source 600. A compound-eye camera may be used as the image sensor 602. Such a compound-eye camera is provided with multiple image sensors and is capable of measuring the distance based on a parallax difference between multiple images acquired. As described above, the image sensor 602 may be a device which can acquire both image information and distance information.

Next, the irradiation adjustment operation to be conducted by the control circuit 114 will be described. The control circuit 114 determines the position on the head 102 to be irradiated with the light and the power of the light on the basis of the specified position and distance of the head 102. For example, the control circuit 114 controls a not-illustrated optical element such as an MEMS mirror such that the light is properly emitted to the specified position on the head 102. Then, the control circuit 114 causes the light source 600 to emit the light such that the power of the light reaching the image sensor 602 substantially has a prescribed value. For example, the control circuit 114 increases the power of the light emitted from the light source 600 as the distance to the head 102 is larger, or decreases the power of the light emitted from the light source 600 as this distance is smaller.

The control circuit 114 performs the above-described operation firstly at the time of staring detection of biological information (at the time of an initial operation), for example. Thus, the light at the appropriate power is emitted to the head 102 so that the biological information can be detected at high accuracy.

After the aforementioned initial operation, the control circuit 114 performs a measurement operation of the biological information.

The control circuit 114 irradiates the head 102 with the light from the light source 600. Light reflected and scattered (which is expressed as "return light") from the head 102 irradiated with light 121 reaches the image sensor 602. The return light includes a component (a surface-reflected light component 606) reflected from a surface of the head 102, and a component (an internally scattered light component 608), which is subjected to any of reflection (inclusive of diffuse reflection) once inside the head 102, scattering, and multiple scattering inside the head 102. Of the components, the internally scattered light component 608 is a target component for detection.

However, the internally scattered light component 608 generally has a small light intensity due to the following reasons. Specifically, the emitted light has an extremely small light quantity so as to satisfy a laser safety standard. In addition, the light is significantly scattered or absorbed by the scalp, the cerebrospinal fluid, the skull, the gray matter, the white matter, and the blood flows. Furthermore, a change in signal intensity associated with a change in amount of a blood flow or a change in components in the blood flow during the brain activity corresponds to the magnitude at several percent of the signal intensity of the internally scattered light component 608, which is extremely small. Accordingly, it is desirable to detect the internally scattered light component 608 while minimizing the mixing of the surface-reflected light component 606, which is several thousands to several tens of thousands of times as large as the target signal component for detection.

To this end, the image sensor 602 provided with an electronic shutter function is used. The control circuit 114 appropriately controls a shutter timing so as to enable detection of only the internally scattered light component 608. This configuration has been disclosed in Japanese Patent Application No. 2015-122390 Specification, for example.

The signal processing circuit 604 receives a signal concerning the internally scattered light component 608 outputted from the image sensor 602, and separates a reflected component from the shallow part of the subject as well as a reflected component from the deep part of the subject from the received signal. Moreover, the signal processing circuit 604 obtains changes in density of oxidized hemoglobin and deoxidized hemoglobin from acquired information on brightness and darkness, and outputs the brain activity in the form of imaging data by means of computation using the changes in density of oxidized hemoglobin and deoxidized hemoglobin thus obtained.

Embodiment 1

The image pickup apparatus 1001 of Embodiment 1 targets at a light-scattering body like a living body as its subject. Specifically, the image pickup apparatus 1001 detects density distribution conditions and temporal changes of oxidized hemoglobin and deoxidized hemoglobin in the brain to be observed, and constructs the density distribution conditions in the form of two-dimensional images. The image pickup apparatus 1001 removes or reduces blood flows on the scalp, which constitute artifacts, in a contactless manner yet at high speed and high accuracy.

Figure 2:
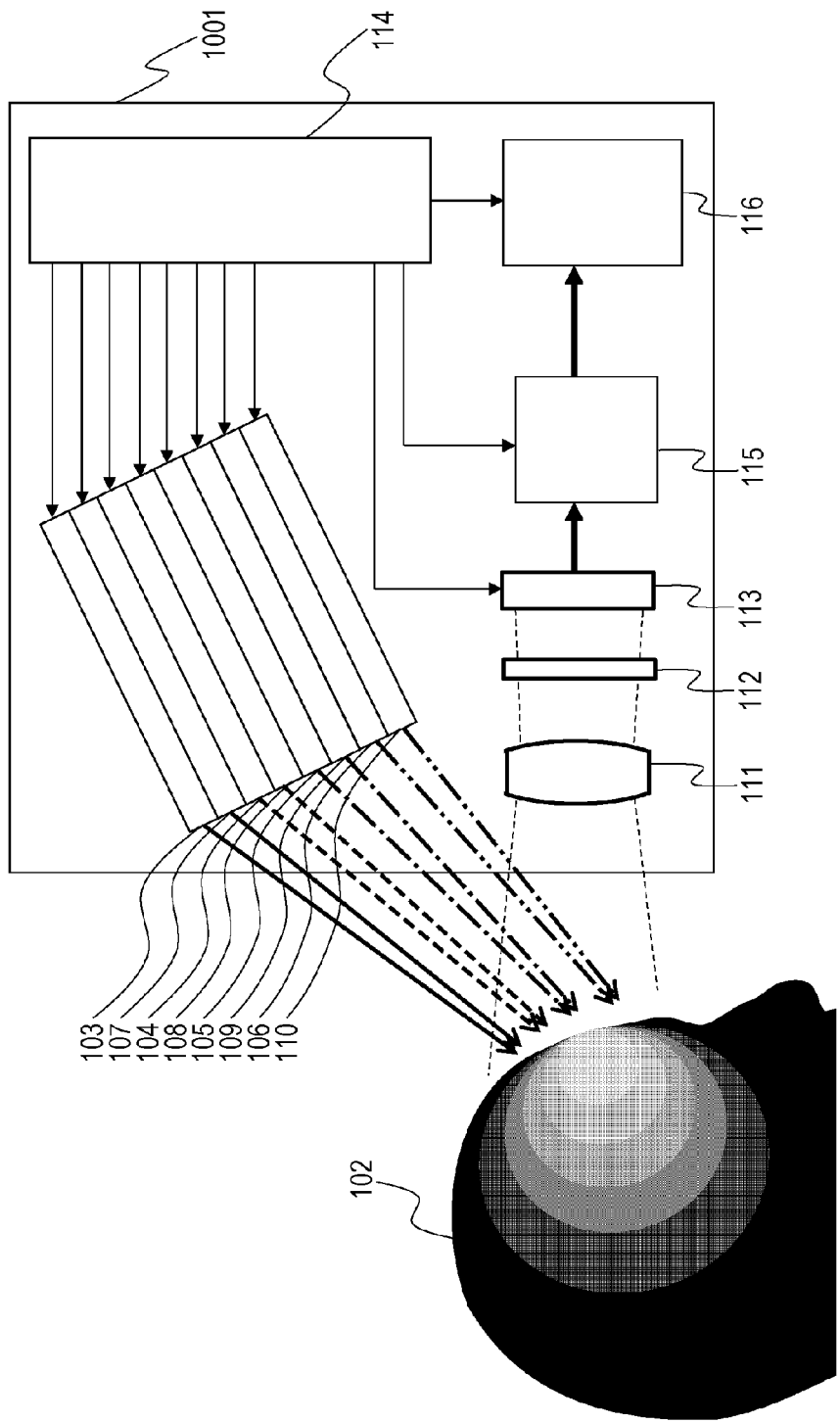
FIG. 2 is an image pickup system diagram including the image pickup apparatus.

FIG. 2 is a diagram showing an image pickup system including the image pickup apparatus 1001 of the Embodiment 1. The use of near infrared light in a range from 700 to 950 nm has been proposed in order to measure densities of oxidized hemoglobin and deoxidized hemoglobin in the brain, because the wavelengths in this range are absorbed relatively less by both body water and hemoglobin in the living body. This wavelength range is referred to as a "biological optical window". Accordingly, the image pickup apparatus 1001 of the Embodiment 1 employs four first light sources 103, 104, 105, and 106 each of which emits pulsed laser light with a wavelength of 750 nm, and four second light sources 107, 108, 109, and 110 each of which emits pulsed laser light with a wavelength of 850 nm, as the light source 600 (FIG. 1).

Each of the first light sources 103, 104, 105, and 106 as well as the second light sources 107, 108, 109, and 110 performs irradiation at short pulses, high speed, and in a repeated manner with the laser beam in accordance with an after-mentioned predetermined pattern. More details will be described later.

The image pickup apparatus 1001 further includes an imaging optical system 111, an optical double band pass filter 112, a time-resolved image sensor 113, the control circuit 114, a first signal processing circuit 115, and a second signal processing circuit 116.

The imaging optical system 111 may include a camera lens.

The optical double band pass filter 112 is a filter which allows passage of the light with two center wavelengths of 750 nm and 850 nm. The optical double band pass filter 112 is disposed on an imaging plane of the lens.

The control circuit 114 is an operating processor, for example, which controls pulsed light emission of the first light sources 103, 104, 105, and 106 as well as the second light sources 107, 108, 109, and 110, and an exposure period for light reception with the time-resolved image sensor 113 in the image pickup apparatus 1001. Moreover, the control circuit 114 converts signal charges accumulated as a consequence of the light reception into digital data, and instructs the first signal processing circuit 115 and the second signal processing circuit 116 to process image data thus obtained.

The first signal processing circuit 115 and the second signal processing circuit 116 collectively correspond to the signal processing circuit 604 in FIG. 1. In other words, the signal processing circuit 604 is embodied in the first signal processing circuit 115 and the second signal processing circuit 116. It is to be noted, however, that this is just an example. The signal processing circuit 604 may be embodied in one circuit as shown in FIG. 1.

The first signal processing circuit 115 executes computation to separate a characteristic of reflected light from a scalp blood flow located at the shallow part in the head 102, and to separate a characteristic of reflected light from a cerebral blood flow in the cerebral cortex located at the deep part therein. As a consequence of the computation, the first signal processing circuit 115 outputs the information on brightness and darkness obtained from the cerebral blood flow.

The second signal processing circuit 116 computes the brain activity by using the changes in density of oxidized hemoglobin and deoxidized hemoglobin from the acquired information on brightness and darkness, and outputs the brain activity in the form of imaging data.

Figure 3A:
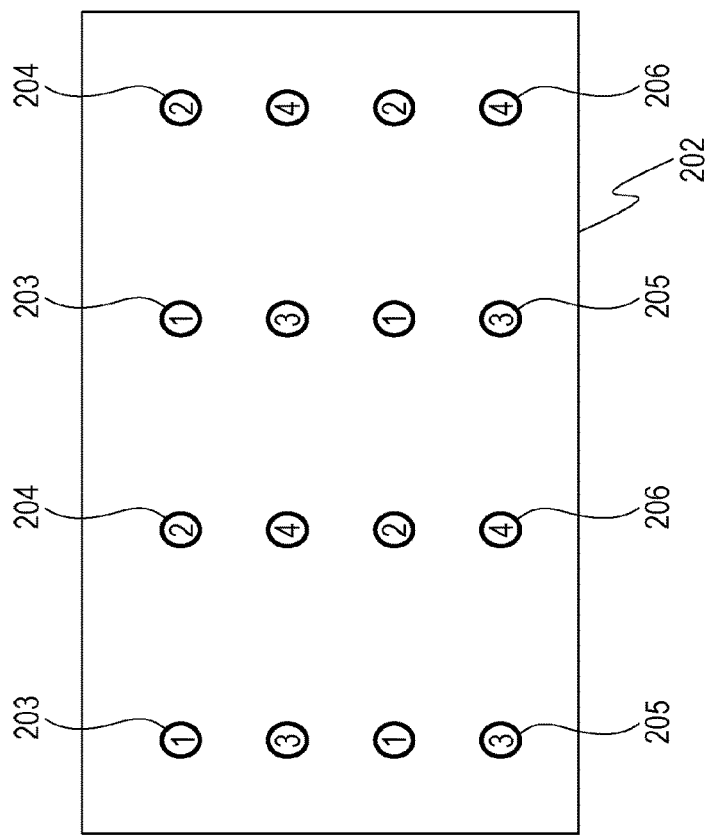
FIG. 3A is a diagram showing a usage scene of the image pickup apparatus of an Embodiment.

FIG. 3A shows a usage scene 200 of the image pickup apparatus 1001 of the Embodiment 1. The image pickup apparatus 1001 is built in a tablet terminal 201. For example, the image pickup apparatus 1001 emits first to fourth irradiation light beams at different time points 1, 2, 3, and 4, respectively. Firstly, light beams with the wavelength of 750 nm are emitted as the first to fourth irradiation light beams from the first light sources 103, 104, 105, and 106. When the light emission is completed, light beams with the wavelength of 850 nm are subsequently emitted from the second light sources 107, 108, 109, and 110. Locations of the first to fourth irradiation light beams are determined in advance such that the respective irradiation light beams are made incident on particular positions of the head 102 (the forehead), thereby forming images of light. A pattern of images to be formed by the irradiation will be referred to as a "light irradiation pattern" in this specification.

Figure 3B:
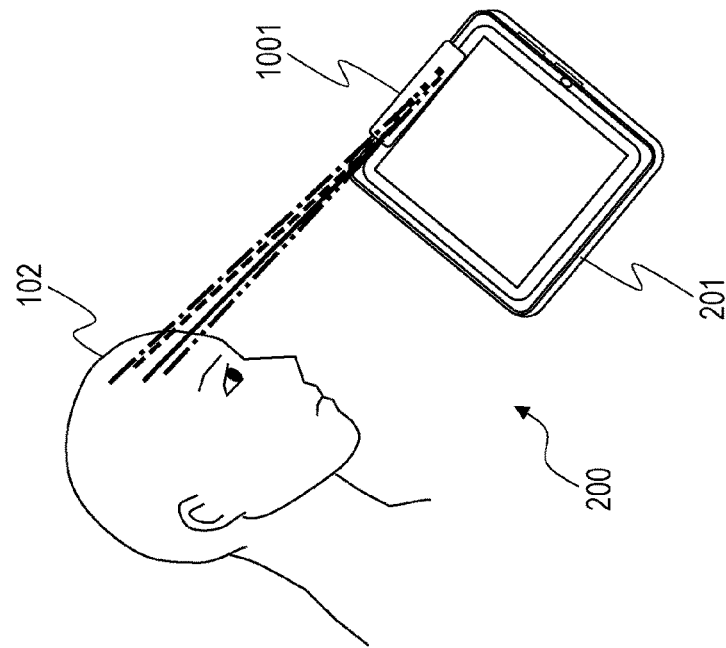
FIG. 3B is a diagram showing an example of a light irradiation pattern to be emitted to a head (a forehead)

FIG. 3B shows an example of a light irradiation pattern 202 to be emitted to the head 102 (the forehead).

Positions 203, 204, 205, and 206 indicated with the circled numbers 1, 2, 3, and 4 in FIG. 3B represent positions of light dots formed on the forehead by the laser beams emitted from the first light sources 103, 104, 105, and 106 as well as the second light sources 107, 108, 109, and 110, respectively. Each array of the light dots formed by the same circled number will be referred to as a "light dot pattern". The light dot pattern represents an example of the light irradiation pattern. For example, the light dots of the laser beam emitted from the first light source 103 are formed at the positions 203. Moreover, the light dots of the laser beam emitted from the second light source 107 at a different timing from the emission from the first light source 103 are also formed at the positions 203. The same applies to the positions 204, 205, and 206. These positions are irradiated in a time-division manner in one frame at operation timings to be described later. The first light source 103 and the second light source 107 form the same light dot pattern. The first light source 104 and the second light source 108 form the same light dot pattern. The first light source 105 and the second light source 109 form the same light dot pattern. The first light source 106 and the second light source 110 form the same light dot pattern.

Here, the "frame" is a unit of output from the image sensor. A signal or data obtained by a certain output operation is equivalent to a signal or data which constitutes one frame.

FIG. 4 is a graph depicting spectral transmittance of the optical double band pass filter 112, which is designed to pass the light components with the wavelengths of 750 nm and 850 nm while shielding light components having other wavelengths. Provision of the optical double band pass filter 112 enables the time-resolved image sensor 113 to effectively acquire the reflected light of the laser beams emitted from the first light sources 103, 104, 105, and 106 as well as the second light sources 107, 108, 109, and 110.

Figure 5:
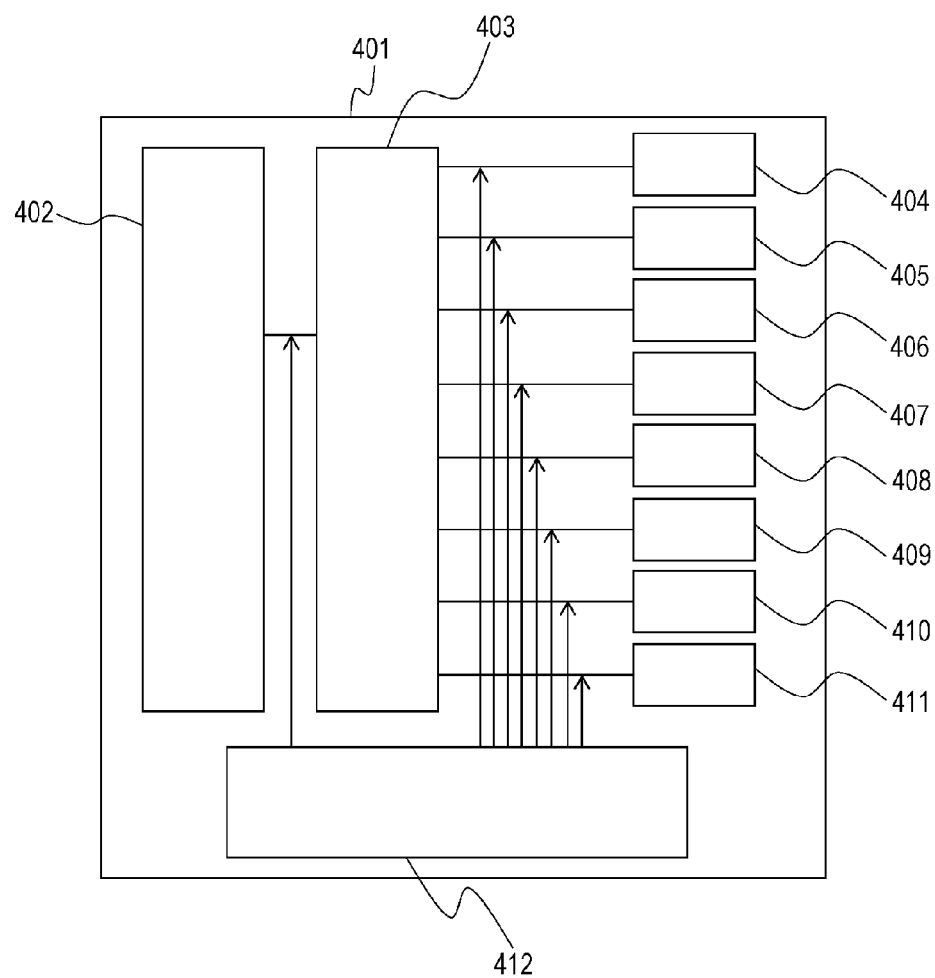
FIG. 5 is a configuration diagram of one pixel in a time-resolved image sensor.

FIG. 5 is a configuration diagram of one pixel 401 in the time-resolved image sensor 113. The one pixel 401 includes: a drain 402 which is a charge release part; a photodetector (PD) 403 which is a photoelectric converter; eight floating diffusion layers (FD) 404, 405, 406, 407, 408, 409, 410, and 411 which are accumulators to accumulate signal charges; and a high speed timing control circuit 412.

The photodetector 403 converts incident photons into signal electrons (signal charges). The high speed timing control circuit 412 outputs control signals and switches whether each signal charge is to be released to the drain 402 or to be accumulated in any one of the floating diffusion layers 404, 405, 406, 407, 408, 409, 410, and 411. The way to determine to which one of the floating diffusion layers 404, 405, 406, 407, 408, 409, 410, and 411 the signal charge is to be accumulated depends on timings to be described later. An operating speed required by these timings is in the order of nanoseconds. To achieve the high speed operations, the high speed timing control circuit 412 is formed of a CMOS logic circuit, for example.

Figure 6:
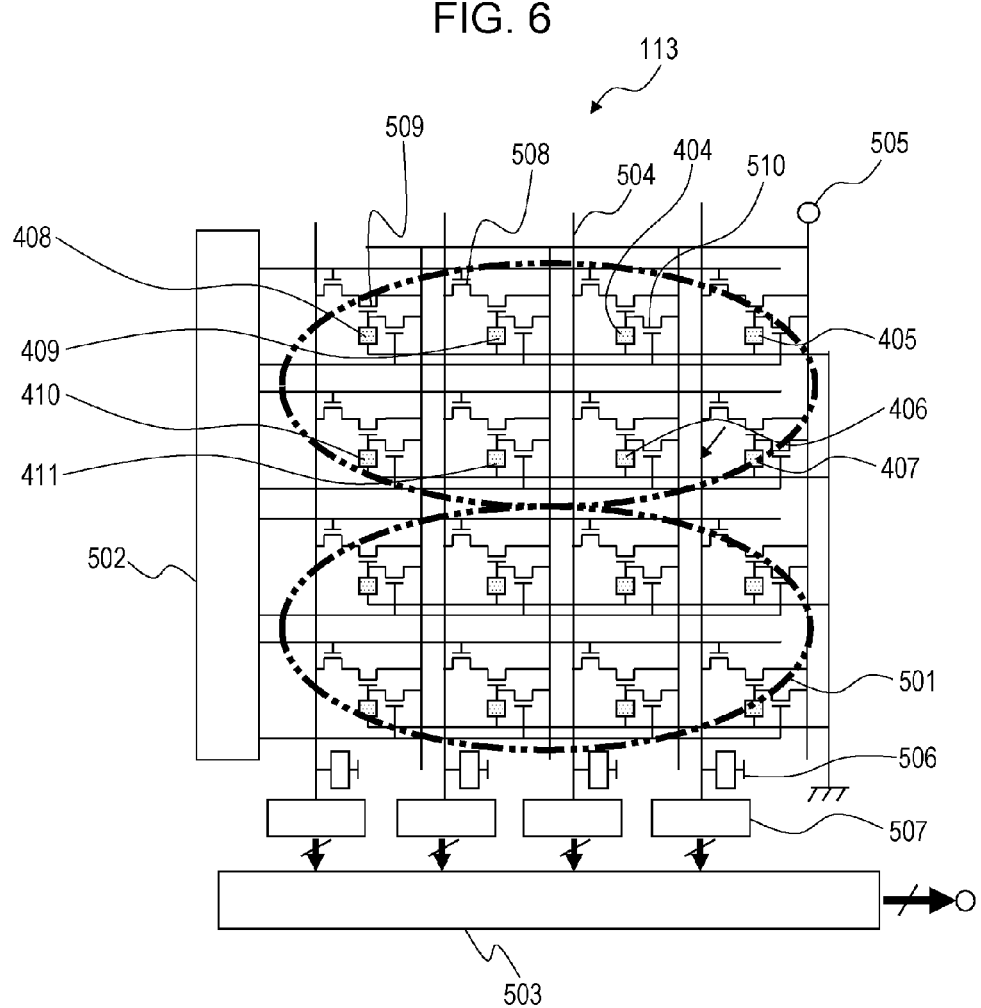
FIG. 6 is a configuration diagram of the time-resolved image sensor of the Embodiment.

FIG. 6 is a configuration diagram of the time-resolved image sensor 113 of the Embodiment 1. A one-pixel region 501 is a region surrounded by a circle in a chain double-dashed line, which includes the eight floating diffusion layers 404, 405, 406, 407, 408, 409, 410, and 411. In the one-pixel region 501, electric charges accumulated therein are treated as if they are signals corresponding to eight pixels (in two rows and four columns) of a typical CMOS image sensor, and are outputted from the time-resolved image sensor 113.

The time-resolved image sensor 113 is actually formed by arranging the circular regions surrounded by the chain double-dashed lines in m rows and n columns horizontally and vertically. However, the Embodiment 1 will be explained with a simple example including the regions in two rows and one column for the convenience of illustrative description.

Basic operations of the image sensor 113 are briefly described below. For the convenience of the description, each remark corresponding to a "floating diffusion layer" may be abbreviated and simply stated as "FD" when appropriate.

Note that illustration of the drain 402, the photodetector 403, and the high speed timing control circuit 412 as appearing in FIG. 5 is omitted in FIG. 6, because the aforementioned constituents are not directly related to a low speed reading operation, in which the signal charge in each floating diffusion layer is outputted from the time-resolved image sensor 113 after completing the accumulation of the signal charge in each FD.

When a row select circuit 502 turns on a signal read transistor 508, the signal charge accumulated in each floating diffusion layer is amplified through a source follower transistor 509 and a source follower load 506, and is read by a vertical signal line 504. Thereafter, an AD converter 507 installed on each column of the floating diffusion layers converts the read signal into digital signal data. A column select circuit 503 outputs a digital signal from the time-resolved image sensor 113. The time-resolved image sensor 113 outputs the signals on the same row, and then reads the next line. Hence, the time-resolved image sensor 113 reads information from all the floating diffusion layers by conducting similar procedures, and turns on a reset transistor 510 after the reading. Accordingly, all the floating diffusion layers are reset. At the timing to start high speed repeated image pickup of the next frame, the series of the frame operations by the image sensor are completed.

While the Embodiment 1 explains the case of using the CMOS type image sensor, the image sensor may be any of a CCD type image sensor, a single-photon counting element, and an amplification type image sensor (such as an EMCCD and an ICCD) instead.

Next, detailed operations of the image pickup apparatus according to the Embodiment 1 will be described with reference to the system configuration diagram of FIG. 1, a timing chart of FIG. 7A, a timing chart of FIG. 7B, and a timing chart of FIG. 8.

Figure 7A:
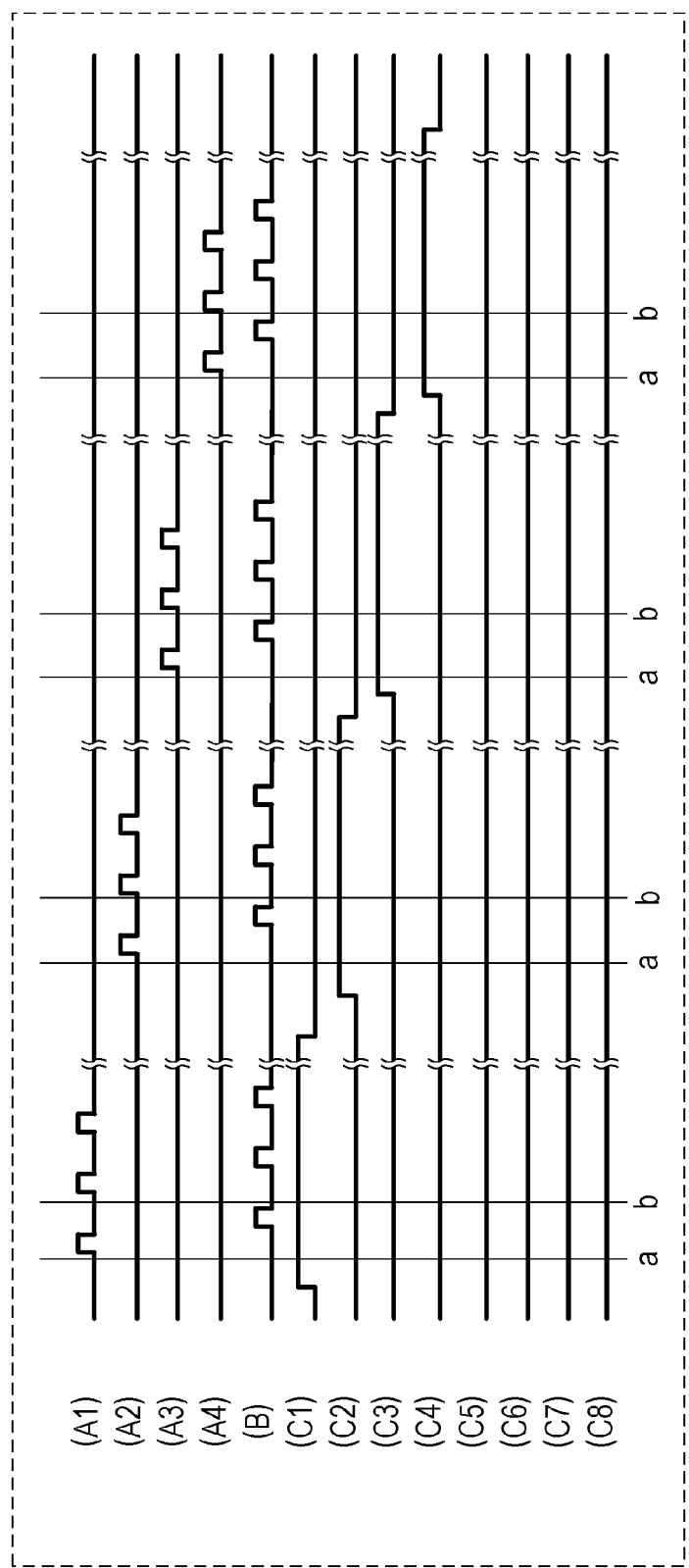
FIG. 7A is a timing chart showing operations of an image pickup apparatus of Embodiment 1.
Figure 7B:
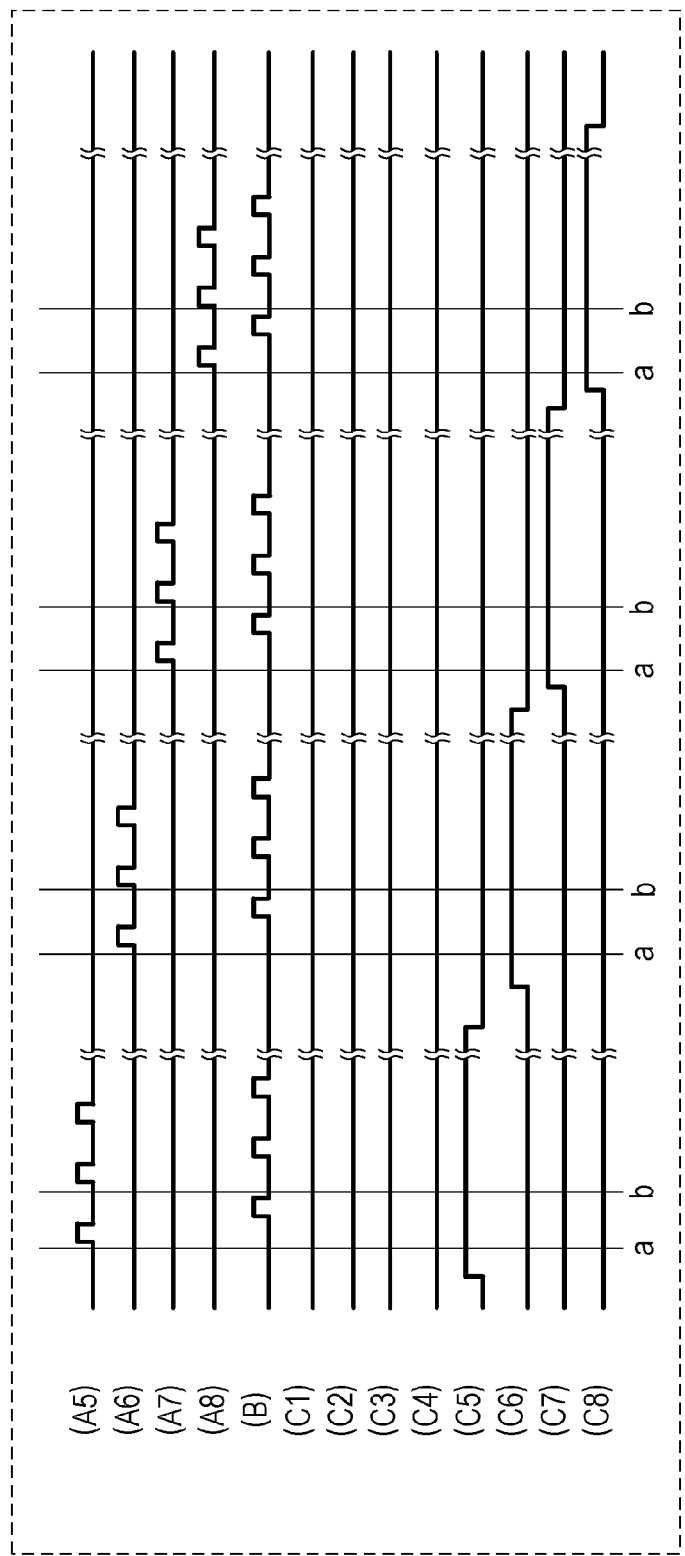
FIG. 7B is another timing chart showing the operations of the image pickup apparatus of the Embodiment 1.

In FIGS. 7A and 7B, signals A1, A2, A3, A4, A5, A6, A7, and A8 indicate light emission timings from the first light sources 103, 104, 105, and 106 as well as the second light sources 107, 108, 109, and 110, respectively. A signal B therein indicates timings to open and close the electronic shutter. Signals C1, C2, C3, C4, C5, C6, C7, and C8 indicate timings to turn the floating diffusion layers 404, 405, 406, 407, 408, 409, 410, and 411 on (i.e., a state where the electric charges are accumulated in the floating diffusion layers) and off (i.e., a state where the electric charges are not accumulated in the floating diffusion layers), respectively. Meanwhile, in FIG. 8, a signal A indicates a light emission timing of a light source, a signal B indicates timings to open and close the electronic shutter, a signal D indicates an intensity of a surface-reflected light component reaching the time-resolved image sensor 113, a signal E indicates an intensity of an internally scattered light component reaching the time-resolved image sensor 113, and a signal F indicates a sum of the signal D and the signal E.

The control circuit 114 in FIGS. 1 and 2 causes the first light source 103 to emit light multiple times at a pulse width of about 10 ns and at a frequency of about 10 MHz as shown in FIG. 7A. The irradiation is usually repeated about 1000 times in a period of about 100 µsec, for example. Although FIG. 7A depicts as if the first light source 103 performs light emission of three pulses, for example, FIG. 7A actually teaches that this pulsed light emission is performed about 1000 times in a period of about 100 µsec. As a consequence of the light emission, a prescribed light image (an irradiation dot pattern) is formed on the head 102 (the forehead). This irradiation dot pattern is formed at the positions on the forehead indicated with the circled number 1 in FIG. 3B. Intervals between the positions indicated with the circled number 1 are set to about 6 cm, for example.

As shown in FIG. 1, the major part of the light component with the wavelength of 750 nm emitted to each position on the forehead indicated with the circled number 1 is reflected from the surface of the head 102. The reflected light is made incident as the return light on the imaging optical system 111 which is the camera lens. A portion of the light component not reflected from the surface of the head 102 reaches the cerebral cortex while being scattered inside the head 102. Then, the portion of the light component having reached the cerebral cortex further continues scattering, and a small amount of this light component again reaches the surface of the forehead of the head 102 as the internally scattered light component. An even smaller portion of the light component emitted from the surface of the forehead of the head 102 to the outside is made incident on the imaging optical system 111, and reaches the time-resolved image sensor 113 where the photoelectric conversion takes place. The light component incident on the imaging optical system 111 includes the surface-reflected light component 606 (FIG. 1), the internally scattered light component 608 (FIG. 1), and ambient light components with wavelengths other than 750 nm and 850 nm. Among them, the ambient light components with wavelengths other than 750 nm and 850 nm are cut off by the optical double band pass filter 112.

As a result, energy of the internally scattered light reaching the time-resolved image sensor 113 is attenuated to about 1/10000 as large as energy of the surface-reflected light reaching the time-resolved image sensor 113. The information on the brain activity is contained in the attenuated light. Accordingly, an important issue here is how to detect the internally scattered light while removing the surface-reflected light that is high energy noise.

A mechanism to solve the issue will be described below with reference to FIG. 8.

Figure 8:
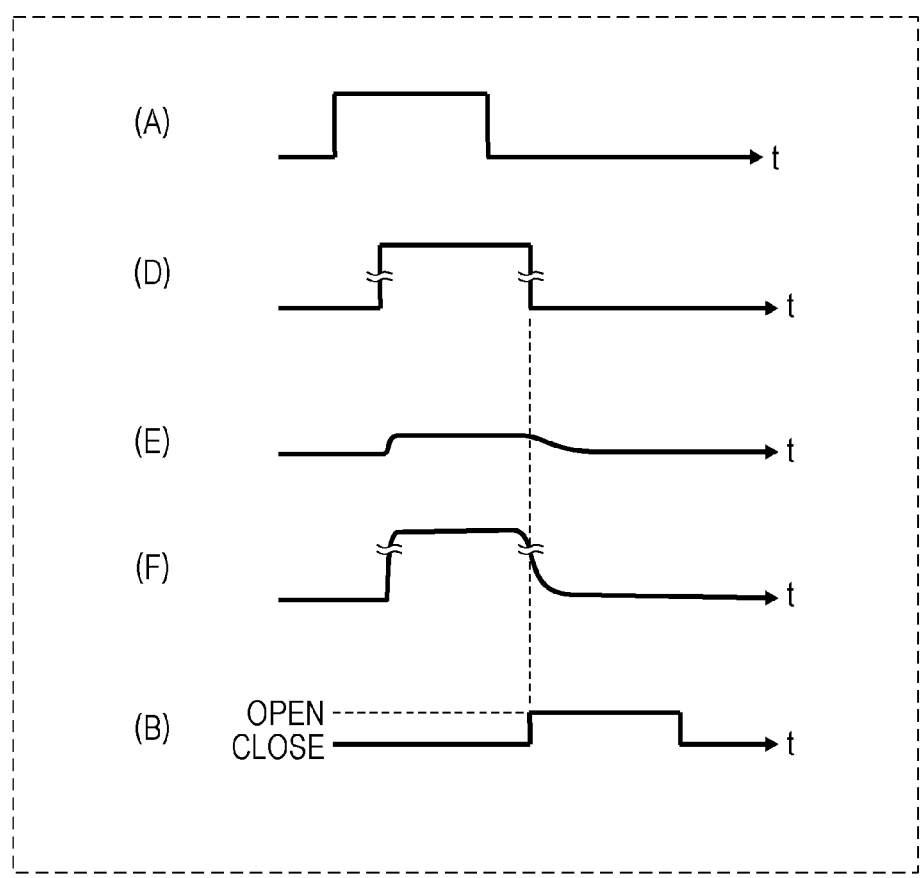
FIG. 8 is a timing chart showing detailed operations of the image pickup apparatus of the Embodiment 1.

FIG. 8 shows details of the timings in each a-b segment in FIGS. 7A and 7B.

As shown in FIG. 8, as a consequence of release control of unnecessary electric charges to the drain 402 conducted by the high speed timing control circuit 412 (FIG. 5), the time-resolved image sensor 113 performs control so as to close the electronic shutter during a period when the electric charges are released to the drain, and to open the electronic shutter during a period when the electric charges are not released to the drain. The high speed timing control circuit 412 sets a time point to start opening the electronic shutter around the time point of disappearance of the surface-reflected light component, so as to detect a larger amount of the internally scattered light while eliminating the surface-reflected light. As compared to the surface-reflected light component, the time point when the internally scattered light is made incident on the time-resolved image sensor 113 is delayed by an amount of time consumed for the scattering. The internally scattered light can be detected at or after the time point of disappearance of the surface-reflected light component.

The time point of disappearance of the surface-reflected light component takes place after a lapse of a certain period from the emission from the corresponding pulsed laser light source. To be more precise, the time point of disappearance of the surface-reflected light component takes place after a lapse of a period from the time point of emission of the laser light from the pulsed laser light source as a starting point, to the time when the surface-reflected light component 606, which originates from the laser light having reached the surface of the forehead of the head 102 and been reflected from the surface of the forehead, is made incident on the time-resolved image sensor 113. In the Embodiment 1, the electronic shutter is opened after a lapse of about 100 picoseconds from the time point of disappearance of the surface-reflected light component. The high speed timing control circuit 412 performs the control such that an open period of the electronic shutter is maintained for a period corresponding to a width of the emitted pulse, and the electronic shutter is closed immediately thereafter.

As the first light source 103 (FIG. 2) emits the pulsed light repeatedly, the electric shutter is also operated in response to the light emission from the first light source 103 as shown in FIG. 7A.

During the period of light emission from the first light source 103, only the floating diffusion layer 404 out of the floating diffusion layers 404, 405, 406, 407, 408, 409, 410, and 411 in FIG. 5 configured to accumulate signal charges is activated by the high speed timing control circuit 412 while the rest of the floating diffusion layers are turned off. In this way, the signal charges for the effective period by opening the electronic shutter are accumulated only in the floating diffusion layer 404. Note that this device is designed such that all the electric charges in the photodetector are released to the drain when the release to the drain is active.

The control circuit 114 opens the electronic shutter at a time point after the surface-reflected light component disappears from an imaging plane of the image sensor and only the internally scattered light is present on the imaging plane of the image sensor, and then the generated signal charges are accumulated in the floating diffusion layer. Thus, it is possible to efficiently remove the surface-reflected light and to detect only the internally scattered light containing the information on the brain activity.

In the case of detecting information such as the cerebral blood flow from the human head 102 as the subject, the attenuation rate of the light inside the subject is extremely large. As described previously, the energy of the internally scattered light is attenuated to about $1/10000$ as large as the energy of the surface-reflected light. In terms of the light quantity, irradiation with just one pulse is insufficient for detecting only the internally scattered light. Accordingly, in the Embodiment, the pulsed light source is caused to emit the light multiple times, while the image sensor performs exposure multiple times by using the electric shutter in response to the light emission. Then, signals thus detected are integrated to enhance sensitivity. Thus, it is possible to detect the information such as the cerebral blood flow in a contactless manner at last.

Next, the control circuit 114 in FIGS. 1 and 2 causes the first light source 104 to emit light multiple times at the pulse width of about 10 ns and at the frequency of about 10 MHz likewise as shown in FIG. 7A. The irradiation dot pattern of the light includes light dots at the positions on the forehead indicated with the circled number 2 in FIG. 3B. In the Embodiment 1, the irradiation is repeated about 1000 times in a period of about 100 μsec, for instance. Thus, the irradiation pattern including the light dots is formed repeatedly on the forehead indicated. Intervals between the positions indicated with the circled number 2 are set to about 6 cm, for example, in such a way as to coincide with intermediate points between the positions indicated with the circled number 1.

Behaviors in a period after the first light source 104 emits light until the internally scattered light reaches the time-resolved image sensor 113 are the same as those in the precedent example, and description thereof will therefore be omitted.

As the first light source 104 emits the pulsed light repeatedly, the electric shutter is also operated in response to the light emission from the first light source 104 as shown in FIG. 7A.

At this time, only the floating diffusion layer 405 out of the floating diffusion layers 404, 405, 406, 407, 408, 409, 410, and 411 in FIG. 5 configured to accumulate signal charges is activated by the high speed timing control circuit 412 while the rest of the floating diffusion layers are turned off. In this way, the signal charges for the effective period by opening the electronic shutter are accumulated only in the floating diffusion layer 405.

Thereafter, the first light source 105 and the first light source 106 are operated likewise as shown in FIG. 7A.

In this way, the signal charges are independently accumulated as described below.

As a consequence of causing the first light source 103 to perform the pulsed light emission in accordance with the irradiation pattern indicated with the circled number 1, the signal charges originating from the internally scattered light are accumulated in the floating diffusion layer 404.

As a consequence of causing the first light source 104 to perform the pulsed light emission in accordance with the irradiation pattern indicated with the circled number 2, the signal charges originating from the internally scattered light are accumulated in the floating diffusion layer 405.

As a consequence of causing the first light source 105 to perform the pulsed light emission in accordance with the irradiation pattern indicated with the circled number 3, the signal charges originating from the internally scattered light are accumulated in the floating diffusion layer 406.

As a consequence of causing the first light source 106 to perform the pulsed light emission in accordance with the irradiation pattern indicated with the circled number 4, the signal charges originating from the internally scattered light are accumulated in the floating diffusion layer 407.

Subsequently, the second light sources 107, 108, 109, and 110 are operated likewise as shown in FIG. 7B. In this way, the signal charges are independently accumulated as described below.

As a consequence of causing the second light source 107 to perform the pulsed light emission in accordance with the irradiation pattern indicated with the circled number 1, the signal charges originating from the internally scattered light are accumulated in the floating diffusion layer 408.

As a consequence of causing the second light source 108 to perform the pulsed light emission in accordance with the irradiation pattern indicated with the circled number 2, the signal charges originating from the internally scattered light are accumulated in the floating diffusion layer 409.

As a consequence of causing the second light source 109 to perform the pulsed light emission in accordance with the irradiation pattern indicated with the circled number 3, the signal charges originating from the internally scattered light are accumulated in the floating diffusion layer 410.

As a consequence of causing the second light source 110 to perform the pulsed light emission in accordance with the irradiation pattern indicated with the circled number 4, the signal charges originating from the internally scattered light are accumulated in the floating diffusion layer 411.

The series of the operations mentioned above are defined as one set, and multiple sets of the operations are repeated within one frame until the required signal charges are accumulated. Time required for accumulating the data corresponding to one set is around 800 μsec, which is quite fast. For example, the time required for repeating several tens of sets of the operations just requires several tens of milliseconds.

When one frame is regarded as an accumulation period of the signal charges, pseudo-synchronization of the irradiation with the first light sources 103, 104, 105, and 106 as well as the second light sources 107, 108, 109, and 110 can be achieved by repeating the operations as described above.

Next, the time-resolved image sensor 113 carries out an operation to read the signal charges accumulated in the floating diffusion layers 404, 405, 406, 407, 408, 409, 410, and 411. The first and second light sources are basically turned off at the time of the reading operation. Details of the reading operation have been described with reference to FIG. 6.

The inventors of the present disclosure have used the above-mentioned two wavelengths because light absorption coefficients of oxidized hemoglobin and deoxidized hemoglobin are reversed at 805 nm. Accordingly, it is possible to detect a change in density of each of oxidized hemoglobin and deoxidized hemoglobin more accurately as compared to the case of using one wavelength.

Note that the two wavelengths (750 nm and 850 nm) of the pulsed laser light sources described so far merely represent one example. It is only necessary to select wavelengths in a wavelength range from 700 to 950 nm, one of which is shorter than 805 nm and the other one of which is longer than 805 nm.

Figure 9A:
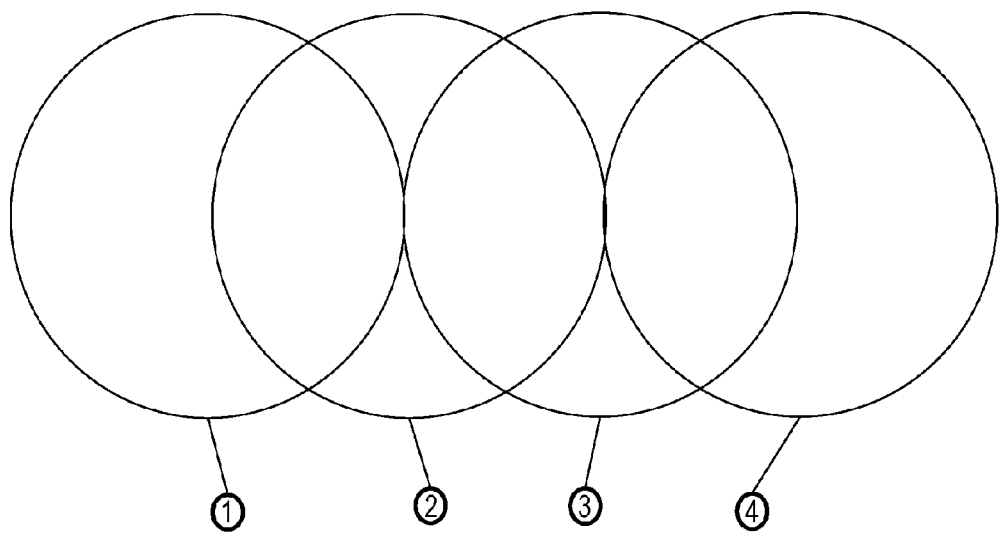
FIG. 9A is a diagram showing an example of a ring-shaped irradiation pattern.
Figure 9B:
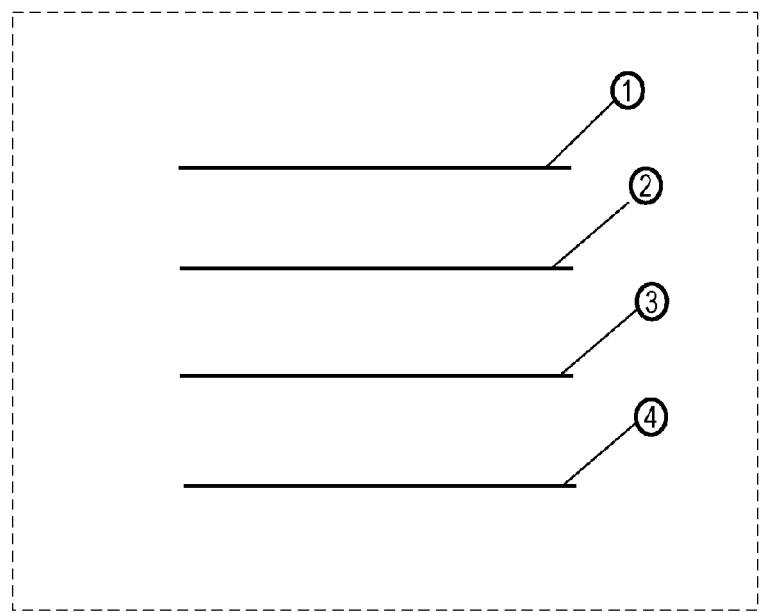
FIG. 9B is a diagram showing an example of a line-shaped irradiation pattern.

The Embodiment 1 has described the case where the light irradiation pattern is formed of the light dot pattern. However, the light irradiation pattern may employ a ring-shaped or line-shaped pattern instead. For instance, FIG. 9A shows an example of a ring-shaped irradiation pattern, and FIG. 9B shows an example of a line-shaped irradiation pattern. Portions in each pattern indicated with the circled numbers 1 to 4 represent images to be formed by the first light sources 103, 104, 105, and 106 as well as the second light sources 107, 108, 109, and 110, respectively. A diameter of each ring shown in FIG. 9A is set to about 6 cm, for example. In the meantime, an interval between the centers of two rings corresponding to two consecutive circled numbers is set to about 3 cm, for example. An interval between two lines indicated in FIG. 9B is set to about 3 cm, for example.

Next, the first signal processing circuit 115 performs separation of the shallow part and the deep part by use of data for eight images outputted from the time-resolved image sensor 113. Each of the eight images corresponds to the signal charges which are accumulated in the corresponding one of the floating diffusion layers 404, 405, 406, 407, 408, 409, 410, and 411, and are acquired in accordance of the corresponding irradiation pattern using the two wavelengths. As for the separation method, there have been known a method of solving simultaneous equations by using light reception data on multiple SD (source—detector; light transmission—light reception) distances as described in JP 2012-125370 A, a subtraction method using an adaptive filter, and so forth.

Figure 10:
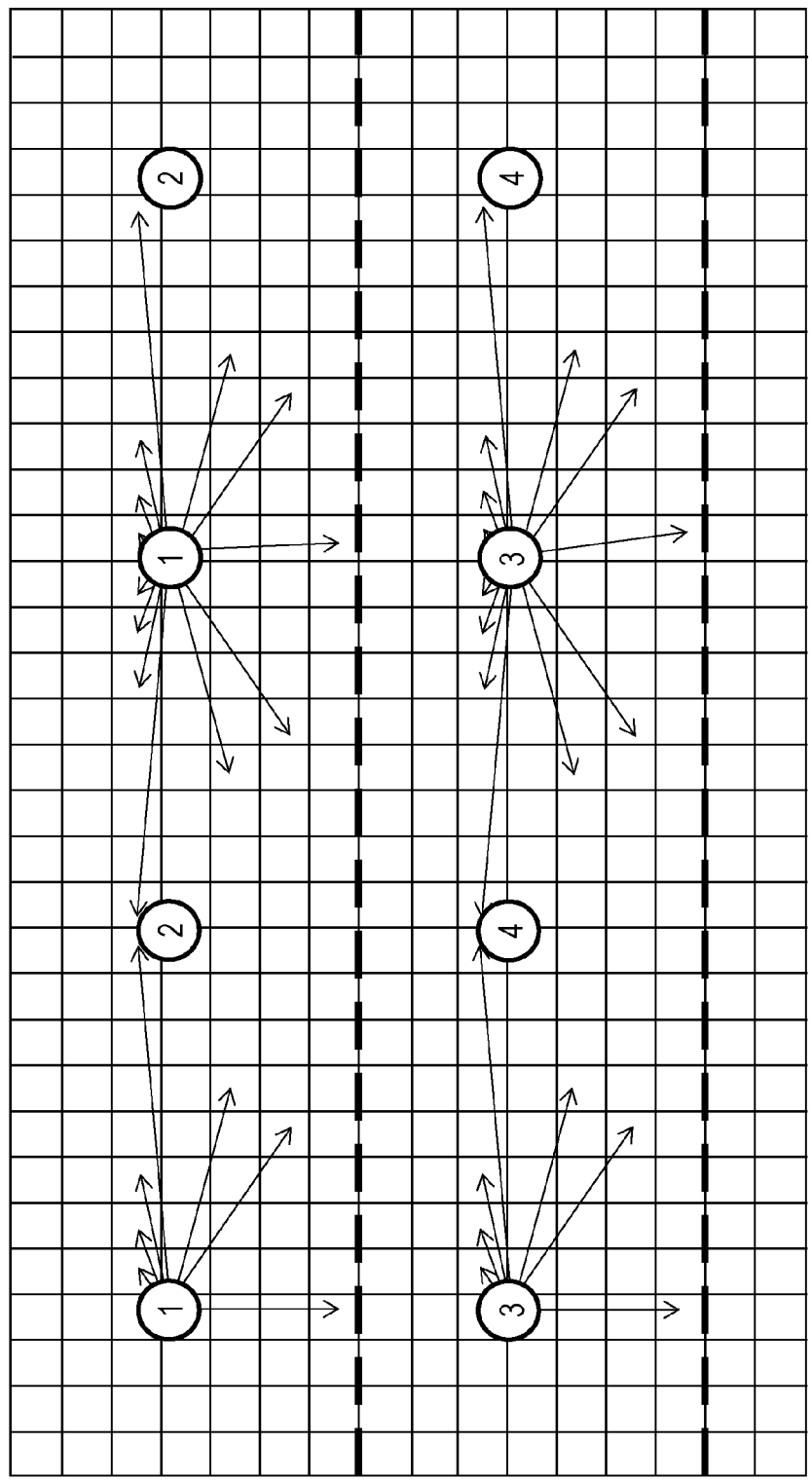
FIG. 10 is a diagram showing relations between a dot irradiation pattern and pixel positions on the time-resolved image sensor in the Embodiment 1.

In the Embodiment, combinations of distances between all the pixels of the image sensor and light irradiation points in every dot pattern are made available as shown in FIG. 10 by using time-division light pattern irradiation and the time-resolved image sensor. Thus, it is possible to acquire numerous SD distance data.

FIG. 10 shows relations between the dot irradiation pattern and pixel positions on the time-resolved image sensor 113. Quadrille grids in FIG. 10 represent the pixel positions of the image sensor corresponding to the surface of the forehead of the subject, while circled numbers 1 to 4 represent positions of irradiation patterns with respective laser pulses. For example, a point of each allow extending from the circled number 1 indicates a position where a laser pulse incident on the position of the circled number 1 emerges again as the internally scattered light component on the surface of the forehead. It is to be noted, however, that the arrows only show certain examples. The internally scattered light components may emerge on positions in various directions around the position of the circled number 1. Such an internally scattered light component may also be detected at a pixel distant from the position of irradiation with the laser pulse. Here, internally scattered light components originating from two positions indicated with the circled number 1 may severally reach positions near the circled number 2 located in between. Accordingly, information on both of the internally scattered light components may be contained in the floating diffusion layer 404 or the floating diffusion layer 408 at the pixels of the aforementioned positions. It is to be also noted that illustration of arrows representing the internally scattered light components related to the circled numbers 2 and 4 in FIG. 10 is omitted for the sake of simplifying the description.

Using the information obtained from the floating diffusion layers 404, 405, 406, 407, 408, 409, 410, and 411 at each pixel, it is possible to acquire information on the internally scattered light components attributed to the light irradiation dot patterns at four different positions, and the signals at steps each corresponding to a distance defined by (the length of the subject/the number of pixels of the image sensor). For example, in the case where the image sensor has 200 pixels in its horizontal direction and the subject has a horizontal length of 20 cm, then it is possible to acquire the signals of the SD distances of each dot pattern by the 1-mm step. This makes it possible to enhance accuracy to separate the shallow part and the deep part. Moreover, the use of the high speed time-resolved image sensor enables high speed image pickup in one frame.

After the first signal processing circuit 115 performs the separation of the shallow part and the deep part at 750 nm and 850 nm, respectively, the second signal processing circuit 116 computes relative changes in oxidized hemoglobin and deoxidized hemoglobin in each pixel from the images of the deep part separated at the two wavelengths while using the light absorption coefficients of oxidized hemoglobin and deoxidized hemoglobin at the respective wavelengths. Thus, it is possible to provide the brain activity imaging at high speed and high accuracy.

The time-resolved image sensor of the Embodiment 1 includes the eight floating diffusion layers per pixel. Accordingly, the number of pixels therein may be fewer than that of an ordinary camera in the case where the subject is a light-scattering body, because a spatial frequency of optical resolution obtainable therefrom is low. Assuming that the image area is the same, each pixel can be designed in a larger size. Hence, this image sensor is highly reasonable.

Figure 11:
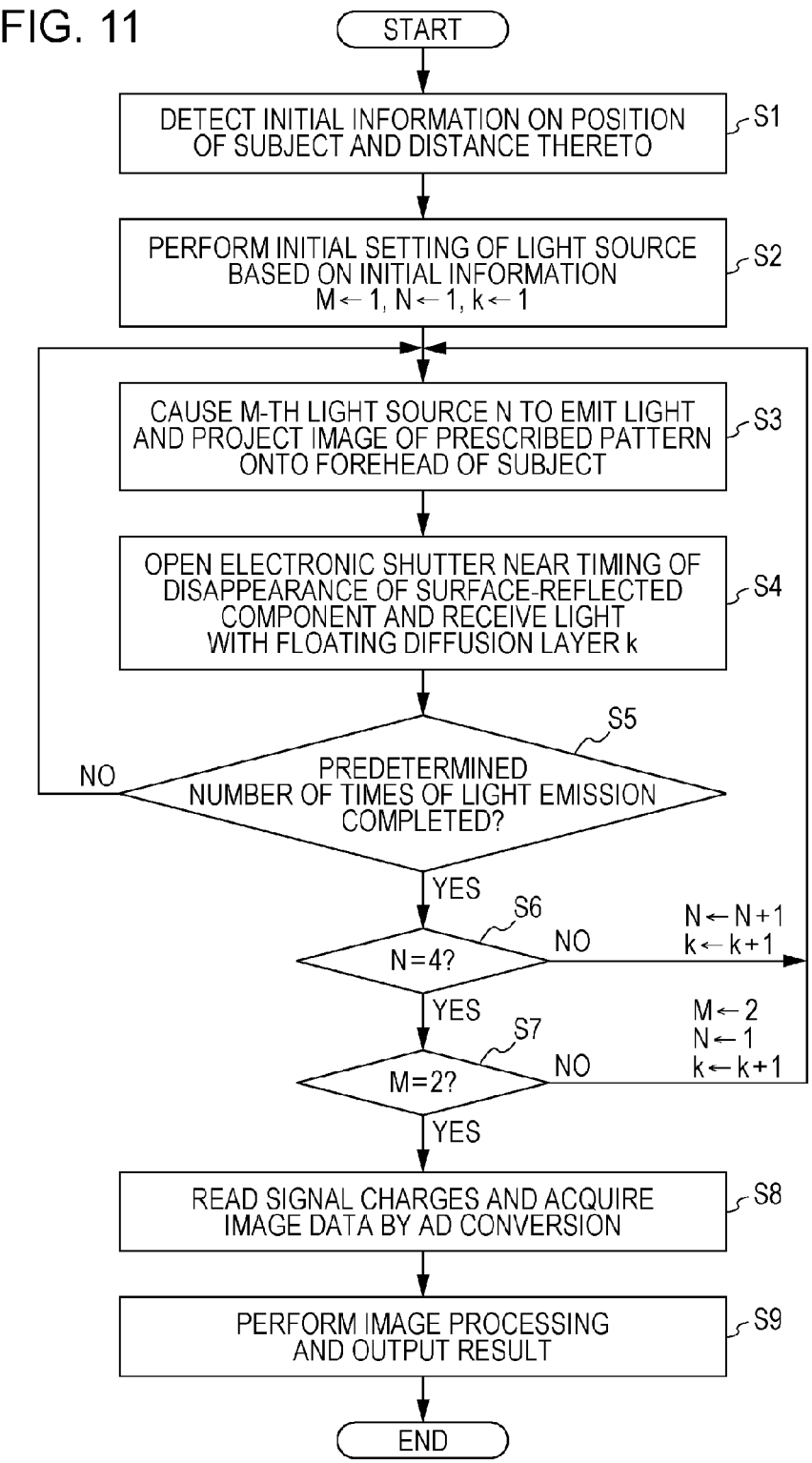
FIG. 11 is a flowchart showing procedures of processing by the image pickup apparatus.

FIG. 11 is a flowchart is showing procedures of processing by the image pickup apparatus 1001. Here, the description is made on the assumption that the control circuit 114 (FIGS. 1 and 2) is an agent of action, which outputs instructions to other constituents. Note that the processing in FIG. 11 represents an example of acquiring the data corresponding to one set.

First, the control circuit 114 detects the position of the head 102 (such as the forehead) of the subject and the distance between the forehead and each of the first light sources 103, 104, 105, and 106 as well as the second light sources 107, 108, 109, and 110 (step S1). Specifically, the control circuit 114 acquires positional information on the forehead in a frame image by means of image recognition while using a video image formed from two or more frame images outputted from the time-resolved image sensor 113. At this time, the time-resolved image sensor 113 only needs to perform a general image pickup operation, and does not have to accumulate the signal charges sequentially in the floating diffusion layers 404, 405, 406, 407, 408, 409, 410, and 411.

The position of the forehead is specified by pattern matching using a template associated with the human forehead. The positional information may be information indicating the position of the center of an image in a detected pattern, for example. The template is stored in advance in a not-illustrated memory. The image recognition is not limited to a particular method, but can widely apply publicly known methods. Meanwhile, the control circuit 114 calculates a distance to the subject based on a signal containing information indicating a phase difference in power of light outputted from the time-resolved image sensor 113.

The distance measurement can also be achieved by using the TOF technique. For example, the light pulses are emitted multiple times and each reflected light is sequentially received with each of the floating diffusion layers of the time-resolved image sensor. Otherwise, the distance to the head may be measured directly by measuring the time of flight of the light from the point of emission of the light pulse to the point of reception of the reflected light.

The control circuit 114 controls the first light sources 103, 104, 105, and 106 or the second light sources 107, 108, 109, and 110.

When the image pickup apparatus 1001 starts the measurement of the biological information, the control circuit 114 outputs control signals for light emission to the first light sources 103, 104, 105, and 106 or the second light sources 107, 108, 109, and 110. The power and directions of emission of the light in this case are set to predetermined initial values. The control circuit 114 executes the initial operations and acquires initial information indicating the position and the distance of the subject.

Next, the control circuit 114 sets the initial values of the power and directions of emission of the light to be emitted from each light source based on the initial information (step S2). Each light source emits to the subject the light which has the power corresponding to the initial value. The above-described operations enable the light emission with appropriate power and in an appropriate direction corresponding to the position of the subject facing the image pickup apparatus 1001 regardless of where the position is located.

Furthermore, the control circuit 114 sets a value 1 to each of variables M, N, and k. The value "M" is either 1 or 2, which indicates a value used in an expression such as "an M-th light source" to correspond to the wavelength of the light source. The value "N" is an integer in a range from 1 to 4 inclusive, which indicates a value used in an expression such as "a first light source N" to specify the light source. Here, the first light source 103 corresponds to a "first light source 1", the first light source 104 corresponds to a "first light source 2", the first light source 105 corresponds to a "first light source 3", the first light source 106 corresponds to a "first light source 4", the second light source 107 corresponds to a "second light source 1", the second light source 108 corresponds to a "second light source 2", the second light source 109 corresponds to a "second light source 3", and the second light source 110 corresponds to a "second light source 4", respectively. The value "k" is an integer in a range from 1 to 8 inclusive, which indicates a value used in an expression such as "a floating diffusion layer k" to specify the floating diffusion layer in which the signal charges are accumulated. Here, the floating diffusion layer 404 corresponds to a "floating diffusion layer 1", the floating diffusion layer 405 corresponds to a "floating diffusion layer 2", the floating diffusion layer 406 corresponds to a "floating diffusion layer 3", the floating diffusion layer 407 corresponds to a "floating diffusion layer 4", the floating diffusion layer 408 corresponds to a "floating diffusion layer 5", the floating diffusion layer 409 corresponds to a "floating diffusion layer 6", the floating diffusion layer 410 corresponds to a "floating diffusion layer 7", and the floating diffusion layer 411 corresponds to a "floating diffusion layer 8", respectively.

Next, the control circuit 114 outputs a control signal to cause the M-th light source N to emit the light, thereby projecting an image of a prescribed pattern onto a region of the head 102 of the subject (step 3).

Then, the control circuit 114 sends a control signal to the high speed timing control circuit 412. Thus, the control circuit 114 opens the electronic shutter around the time point of disappearance of the surface-reflected light component, thereby causing the floating diffusion layer k to receive the internally scattered light component (step S4).

Next, the control circuit 114 determines whether or not the M-th light source N is caused to emit the light a predetermined number of times (step S5). Such a predetermined number of times is 1000 times, for example. The processing proceeds to step S6 when the number of times of light emission satisfies the condition. If not, the processing returns to step S3 and the control circuit 114 conducts the light emission and the reception of the internally scattered light component again.

Then, the control circuit 114 determines whether or not the value N is equal to 4 (step S6). In other words, the control circuit 114 determines whether or not the light emission from the first light source 4 has been completed. The processing proceeds to step S7 when the value N is equal to 4. On the other hand, the processing returns to step S3 when the value N is less than 4. In this case, each of the value N and the value k is incremented by 1. Thus, it is possible to change the light source to emit the light next, and to change the floating diffusion layer to be operated for the next light reception.

Next, the control circuit 114 determines whether or not the value M is equal to 2 (step S7). In other words, the control circuit 114 determines whether or not the light emission from the second light source 4 has been completed. The processing proceeds to step S8 when the value M is equal to 2. On the other hand, the processing returns to step S3 when the value N is less than 2 (i.e., M=1). In this case, 2 is assigned to the value M, 1 is assigned to the value N, and the value k is incremented by 1. Thus, it is possible to cause the second light source 1 to emit the light.

Then, the control circuit 114 generates a control signal for reading the signal charges accumulated in the floating diffusion layers 404, 405, 406, 407, 408, 409, 410, and 411 of each pixel 401, and send the control signal to the time-resolved image sensor 113. Thus, the respective signal charges accumulated in the floating diffusion layers 404, 405, 406, 407, 408, 409, 410, and 411 are read out as analog signals. At the same time, the control circuit 114 instructs an AD converter 507 to convert the analog signals thus read out into digital data, thereby acquiring image data (step S8).

Lastly, the control circuit 114 instructs the first signal processing circuit 115 and the second signal processing circuit 116 to separate a characteristic of reflected light from a scalp blood flow located at the shallow part in the head 102, and to separate a characteristic of reflected light from a cerebral blood flow in the cerebral cortex located at the deep part therein. Thus, the control circuit 114 instructs the first signal processing circuit 115 and the second signal processing circuit 116 to generate information on brightness and darkness obtained from the cerebral blood flow, and further to obtain and output the imaging data by computing the brain activity using changes in density of oxidized hemoglobin and deoxidized hemoglobin in the acquired information on brightness and darkness (step S9).

Embodiment 2

Next, Embodiment 2 of the present disclosure will be described. An image pickup apparatus of the Embodiment 2 targets at a light-scattering body like a living body as its subject. Specifically, the image pickup apparatus detects density distribution conditions and temporal changes of oxidized hemoglobin and deoxidized hemoglobin in the brain to be observed, and constructs the density distribution conditions in the form of two-dimensional images.

While the objective of the Embodiment 2 is the same as the objective of the Embodiment 1, the Embodiment 2 applies a method of separating the scalp blood flow at the shallow part and the cerebral blood flow at the deep part, which is different from the method in the Embodiment 1. Specifically, the Embodiment 2 uses an electronic shutter period between two different phases under the same light emission pattern and the same wavelength. By adding a time-resolved method to the multiple SD method, it is possible to separate the scalp blood flow at the shallow part and the cerebral blood flow at the deep part more accurately.

The following description will be given by mainly focusing on different features from the Embodiment 1. Structures and/or functions of constituents not particularly explained herein are the same as those of the configuration of the image pickup apparatus 1001 of the Embodiment 1.

Figure 12:
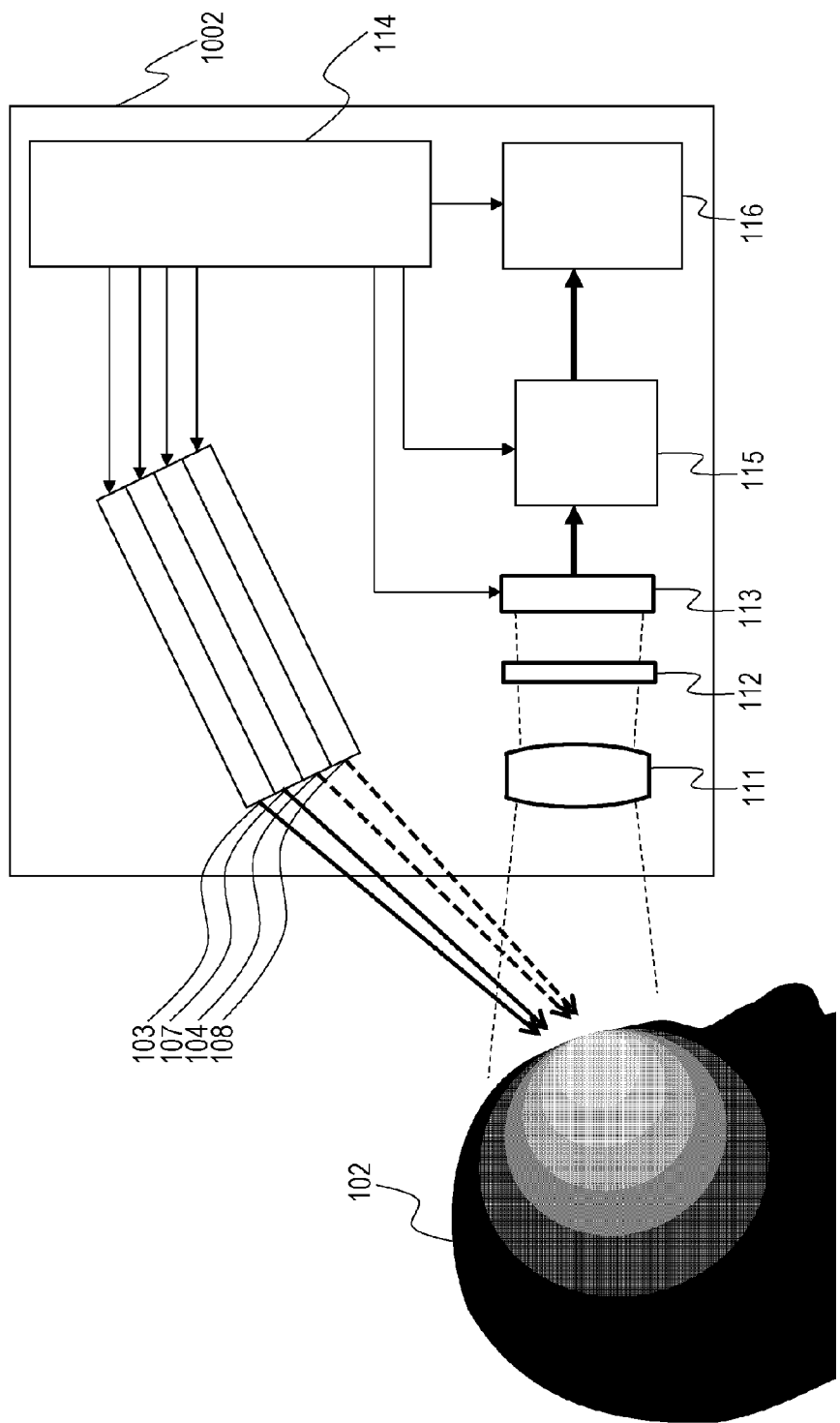
FIG. 12 is an image pickup system diagram including an image pickup apparatus of Embodiment 2.

FIG. 12 is an image pickup system diagram including an image pickup apparatus 1002 of the Embodiment 2.

Different features of the image pickup apparatus 1002 from those of the image pickup apparatus 1001 of the Embodiment 1 include the number of light sources and operations of the time-resolved image sensor 113. Due to these different features, operations of the control circuit 114 are also different. Nonetheless, these apparatuses are the same in terms of hardware. Accordingly, the same names and reference signs are employed herein. Operations of the image pickup apparatus 1002 inclusive of the operations of the control circuit 114 therein will be described below in detail.

The image pickup apparatus 1002 includes two first light sources 103 and 104 each of which emits pulsed laser light with a wavelength of 750 nm, and two second light sources 107 and 108 each of which emits pulsed laser light with a wavelength of 850 nm. Each light source performs irradiation at short pulses, high speed, and in a repeated manner in accordance with a predetermined pattern to be described later.

FIG. 13A shows a usage scene 1200 of the image pickup apparatus 1002 of the Embodiment 2. The image pickup apparatus 1002 is built in a tablet terminal 1201. For example, the image pickup apparatus 1002 emits first and second irradiation light beams at different time points 1 and 2, respectively. Firstly, light beams with the wavelength of 750 nm are emitted as the first and second irradiation light beams from the first light sources 103 and 104. When the light emission is completed, light beams with the wavelength of 850 nm are subsequently emitted from the second light sources 107 and 108. Locations of the respective irradiation light beams are determined in advance such that the respective irradiation light beams are made incident on particular positions of the head 102. In other words, each light irradiation pattern representing a pattern of an image formed by the irradiation is determined in advance.

FIG. 13B shows an example of a light irradiation pattern 1102 to be emitted to the head 102.

Positions 1103 and 1104 indicated with the circled numbers 1 and 2 in FIG. 13B represent positions of light dot patterns formed by the laser beams emitted from the first light sources 103 and 104 as well as the second light sources 107 and 108, 109, and 110, respectively. These positions are irradiated in a time-division manner at different time points in one frame at operation timings to be described later.

In the Embodiment 2, the characteristics of the optical double band pass filter 112, the configuration of each pixel in the time-resolved image sensor 113, and the overall configuration are the same as those illustrated in FIGS. 4 to 6, respectively. Accordingly, duplicate explanations thereof will be omitted.

While the Embodiment 2 also explains the case of using the CMOS type image sensor as the time-resolved image sensor 113, the image sensor may be any of a CCD type image sensor, a single-photon counting element, and an amplification type image sensor (such as an EMCCD and an ICCD) instead.

Detailed operations of the image pickup apparatus according to the Embodiment 2 of the present disclosure will be described below with reference to the system configuration diagram of FIG. 12, a timing chart of FIG. 14A, a timing chart of FIG. 14B, a timing charge of FIG. 15A, and a timing chart of FIG. 15B.

Figure 14A:
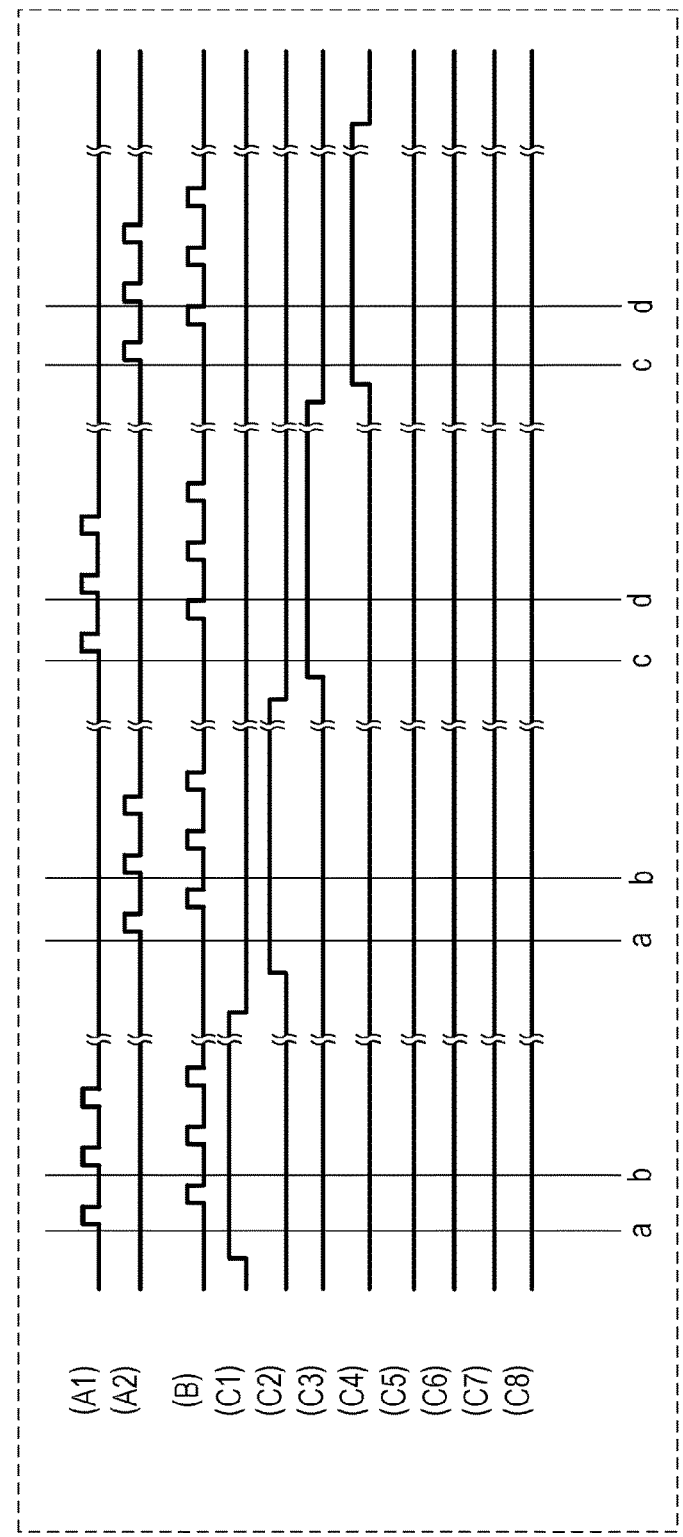
FIG. 14A is a timing chart showing operations of an image pickup apparatus of the Embodiment 2.

In FIGS. 14A and 14B, signals A1, A2, A5, and A6 indicate light emission timings from the first light sources 103 and 104 as well as the second light sources 107 and 108, respectively. A signal B therein indicates timings to open and close the electronic shutter. Signals C1, C2, C3, C4, C5, C6, C7, and C8 indicate timings to turn the floating diffusion layers 404, 405, 406, 407, 408, 409, 410, and 411 on (i.e., the state where the electric charges are accumulated in the floating diffusion layers) and off (i.e., the state where the electric charges are not accumulated in the floating diffusion layers), respectively. Meanwhile, in FIGS. 15A and 15B, a signal A indicates a light emission timing of a light source, a signal B1 indicates timings to open and close the electronic shutter during a period from a time point a to a time point b, a signal B2 indicates timings to open and close the electronic shutter during a period from a time point c to a time point d, a signal D indicates an intensity of a surface-reflected light component reaching the time-resolved image sensor 113, a signal E indicates an intensity of an internally scattered light component reaching the time-resolved image sensor 113, and a signal F indicates a sum of the signal D and the signal E.

The control circuit 114 in FIGS. 1 and 12 causes the first light source 103 to emit light multiple times at a pulse width of about 10 ns and at a frequency of about 10 MHz as shown in FIG. 14A. The irradiation is usually repeated about 1000 times in a period of about 100 μsec, for instance. In this case, the irradiation dot pattern is formed at the positions on the forehead indicated with the circled number 1 in FIG. 13B. For example, intervals between the positions indicated with the circled number 1 are set to about 6 cm in horizontal and vertical directions, and to 8.49 cm in a diagonal direction calculated by multiplying each interval by the "square root of 2".

Behaviors of the light components of the respective wavelengths incident on the forehead, and the principle of detection of the internally scattered light components are the same as those of the Embodiment 1. The degrees of the attenuation of the internally scattered light components are the same as well.

A mechanism to detect the internally scattered light component in the Embodiment 2 will be described below.

FIG. 15A shows details of time points in each a-b segment in FIGS. 14A and 14B.

As shown in FIG. 15A, as a consequence of release control of unnecessary electric charges to a drain conducted by the high speed timing control circuit 412 (FIG. 5), the time-resolved image sensor 113 performs control so as to close the electronic shutter during the period when the electric charges are released to the drain, and to open the electronic shutter during the period when the electric charges are not released to the drain.

Here, FIG. 15B is a timing chart showing an enlarged section around a time point f to a time point g in the timing chart of FIG. 15A. Based on an instruction from the control circuit 114, the high speed timing control circuit 412 sets a time point to start opening the electronic shutter at the time point f immediately after the time of disappearance of the surface-reflected light component. The time point f is around 100 picoseconds after the disappearance of the surface-reflected light component, for example. Moreover, the high speed timing control circuit 412 maintains the open period of the electronic shutter for a period corresponding to a width of the emitted light pulse, and closes the electronic shutter immediately thereafter.

As the first light source 103 emits the pulsed light repeatedly, the electric shutter is also operated in response to the light emission from the first light source 103 as shown in FIG. 14A.

During the period of light emission from the first light source 103, only the floating diffusion layer 404 out of the floating diffusion layers 404, 405, 406, 407, 408, 409, 410, and 411 in FIG. 5 configured to accumulate signal charges is activated by the high speed timing control circuit 412 while the rest of the floating diffusion layers are turned off. In this way, the signal charges for the effective period by opening the electronic shutter are accumulated only in the floating diffusion layer 404. Note that this device is designed such that all the electric charges in the photodetector are released to the drain when the release to the drain is active.

The control circuit 114 opens the electronic shutter at the time point after the surface-reflected light component disappears from an imaging plane of the image sensor and only the internally scattered light is present on the imaging plane of the image sensor, thereby accumulating the generated signal charges in the floating diffusion layer. Thus, it is possible to efficiently remove the surface-reflected light.

As described previously, in the case of detecting information such as the cerebral blood flow from the human forehead as the subject, the attenuation rate of the light inside the subject is extremely large (about 1/10000). For this reason, in terms of the light quantity, irradiation with just one pulse is insufficient for detecting only the internally scattered light. Accordingly, the pulsed light source emits the light multiple times, while the image sensor performs exposure multiple times by using the electric shutter in response to the light emission. Then, signals thus detected are integrated to enhance sensitivity. At last, it is possible to detect the information such as the cerebral blood flow in a contactless manner.

Next, the control circuit 114 in FIGS. 1 and 12 causes the first light source 104 to emit light multiple times at the pulse width of about 10 ns and at the frequency of about 10 MHz as shown in FIG. 14A. In the Embodiment 2, the irradiation is repeated about 1000 times in a period of about 100 μsec, for instance. This irradiation dot pattern is formed at the positions on the forehead indicated with the circled number 2 in FIG. 13B. Intervals between the positions indicated with the circled number 2 are set to about 6 cm, for example, in such a way as to coincide with intermediate points between the positions indicated with the circled number 1.

Operation timings of the electronic shutter are the same as those applicable to the aforementioned section a-b shown in FIG. 15A.

As the first light source 104 emits the pulsed light repeatedly, the electric shutter is also operated in response to the light emission from the first light source 104 as shown in FIG. 14A.

At this time, only the floating diffusion layer 405 out of the floating diffusion layers 404, 405, 406, 407, 408, 409, 410, and 411 in FIG. 5 is activated by the high speed timing control circuit 412 while the rest of the floating diffusion layers are turned off. In this way, the signal charges for the effective period by opening the electronic shutter are accumulated only in the floating diffusion layer 405.

The control circuit 114 opens the electronic shutter at the time point after the surface-reflected light component disappears from the imaging plane of the image sensor, thereby accumulating the generated signal charges in the floating diffusion layer. Thus, it is possible to efficiently remove the surface-reflected light and to detect only the internally scattered light containing the information on the brain activity. Here, it is possible to cause the first light source 104 to emit the light multiple times as well, then to cause the image sensor to perform exposure multiple times by using the electric shutter in response thereto, and thus to integrate detected signals, thereby enhancing sensitivity.

Next, the second round of light emission from the first light source 103 will be described.

The control circuit 114 in FIGS. 1 and 12 causes the first light source 103 to emit light multiple times at the pulse width of about 10 ns and at the frequency of about 10 MHz as shown in FIG. 14A. In the Embodiment 2, the irradiation is repeated about 1000 times in a period of about 100 μsec, for instance. This irradiation dot pattern is formed at the positions on the forehead indicated with the circled number 1 in FIG. 13B.

Operation timings of the electronic shutter are the same as those applicable to the aforementioned section a-b shown in FIG. 15A.

As shown in FIG. 15A, as a consequence of the release control of unnecessary electric charges to the drain conducted by the high speed timing control circuit 412 (FIG. 5), the time-resolved image sensor 113 performs control so as to close the electronic shutter during the period when the electric charges are released to the drain, and to open the electronic shutter during the period when the electric charges are not released to the drain.

FIG. 15A also shows detailed timings in each section c-d in FIGS. 14A and 14B. Specifically, based on an instruction from the control circuit 114, the high speed timing control circuit 412 sets a time point to start opening the electronic shutter at the time point g illustrated in an enlarged portion e after a lapse of nanoseconds (ns) since the disappearance of the surface-reflected light component. The time point g is around 2 to 3 ns after the disappearance of the surface-reflected light component, for example. Moreover, the high speed timing control circuit 412 maintains the open period of the electronic shutter for the period corresponding to the width of the emitted light pulse, and closes the electronic shutter immediately thereafter. The internally scattered light component that returns in this period of a few nanoseconds (an f-g period such as 3 ns) contains more information on the shallow part than information on the deep part due to a short optical path length. In other words, an optical component reaching the image sensor after the time point g exhibits a higher ratio of the information on the deep part since this optical component tends to contain the component representing a long optical path length of the scattered light.

As the first light source 103 emits the pulsed light repeatedly, the electric shutter is also operated in response to the light emission from the first light source 103 as shown in FIG. 14A.

During the period of light emission from the first light source 103, only the floating diffusion layer 406 out of the floating diffusion layers 404, 405, 406, 407, 408, 409, 410, and 411 in FIG. 5 configured to accumulate signal charges is activated by the high speed timing control circuit 412 while the rest of the floating diffusion layers are turned off. In this way, the signal charges for the effective period by opening the electronic shutter are accumulated only in the floating diffusion layer 406.

The signal charge components obtained by opening the electronic shutter starting the time point f contain a sufficiently larger amount of the information on the shallow part than the information on the deep part. As a consequence, the signal charge components contain a sufficiently larger amount of scalp blood flow components than cerebral blood flow components.

On the other hand, as compared to the signal charge components acquired starting the time f, the signal charge components obtained by opening the electronic shutter starting the time point g contain a higher ratio of the information on the deep part, and a ratio of the cerebral blood flow components therein is increased as a consequence.

The inventors of the present disclosure have focused on the importance of a change in ratio as mentioned above depending on the time point to open and close the electronic shutter.

The control circuit 114 opens the electronic shutter at the time point after the surface-reflected light component disappears from the imaging plane of the image sensor and only the internally scattered light is present on the imaging plane of the image sensor, thereby accumulating the generated signal charges in the floating diffusion layer. Thus, it is possible to efficiently remove the surface-reflected light. As mentioned earlier, in terms of the internally scattered light, the ratio of the cerebral blood flow components at the deep part is higher in the signal charges accumulated in the floating diffusion layer 406 than in the signal charges accumulated in the floating diffusion layer 404.

Next, the second round of light emission from the first light source 104 will be described.

The control circuit 114 in FIGS. 1 and 12 causes the first light source 104 to emit light multiple times at the pulse width of about 10 ns and at the frequency of about 10 MHz as shown in FIG. 14A. In the Embodiment 2, the irradiation is repeated about 1000 times in a period of about 100 μsec, for instance. This irradiation dot pattern is formed at the positions on the forehead indicated with the circled number 2 in FIG. 13B.

As shown in FIG. 15A, as a consequence of the release control of unnecessary electric charges to the drain conducted by the high speed timing control circuit 412 (FIG. 5), the time-resolved image sensor 113 performs control so as to close the electronic shutter during the period when the electric charges are released to the drain, and to open the electronic shutter during the period when the electric charges are not released to the drain.

FIG. 15A also shows the detailed timings in each section c-d in FIGS. 14A and 14B. Specifically, based on an instruction from the control circuit 114, the high speed timing control circuit 412 sets a time point to start opening the electronic shutter at the time point g after the lapse of nanoseconds (ns) since the disappearance of the surface-reflected light component. Moreover, the high speed timing control circuit 412 maintains the open period of the electronic shutter for the period corresponding to the width of the emitted light pulse, and closes the electronic shutter immediately thereafter. The internally scattered light component that returns in this period of a few nanoseconds (the f-g period) contains more information on the shallow part than information on the deep part due to the short optical path length. In other words, an optical component reaching the image sensor 113 after the time point g exhibits a higher ratio of the information on the deep part.

As the first light source 104 emits the pulsed light repeatedly, the electric shutter is also operated in response to the light emission from the first light source 104 as shown in FIG. 14A.

During the period of the second round of light emission from the first light source 104, only the floating diffusion layer 407 out of the floating diffusion layers 404, 405, 406, 407, 408, 409, 410, and 411 in FIG. 5 configured to accumulate signal charges is activated by the high speed timing control circuit 412 while the rest of the floating diffusion layers are turned off. In this way, the signal charges for the effective period by opening the electronic shutter are accumulated only in the floating diffusion layer 407.

Accordingly, the signal charge components obtained by opening the electronic shutter starting the time point f contain a sufficiently larger amount of the information on the shallow part than the information on the deep part. As a consequence, the signal charge components contain a sufficiently larger amount of scalp blood flow components than cerebral blood flow components.

As compared to the signal charge components acquired starting the time f, the signal charge components obtained by opening the electronic shutter starting the time point g contain a higher ratio of the information on the deep part, and a ratio of the cerebral blood flow components therein is increased as a consequence.

The control circuit 114 opens the electronic shutter at the time point after the surface-reflected light component disappears from the imaging plane of the image sensor and only the internally scattered light is present on the imaging plane of the image sensor, thereby accumulating the generated signal charges in the floating diffusion layer. Thus, it is possible to efficiently remove the surface-reflected light. As mentioned earlier, in terms of the internally scattered light, the ratio of the cerebral blood flow components at the deep part is higher in the signal charges accumulated in the floating diffusion layer 407 than in the signal charges accumulated in the floating diffusion layer 405.

As a result of the above-described operations, the signal charges are independently accumulated as described below.

As a consequence of causing the first light source 103 to perform the pulsed light emission in accordance with the irradiation pattern indicated with the circled number 1, the signal charges at the phase time point f to open the electronic shutter are accumulated in the floating diffusion layer 404.

As a consequence of causing the first light source 104 to perform the pulsed light emission in accordance with the irradiation pattern indicated with the circled number 2, the signal charges at the phase time point f to open the electronic shutter are accumulated in the floating diffusion layer 405.

As a consequence of causing the first light source 103 to perform the pulsed light emission in accordance with the irradiation pattern indicated with the circled number 1, the signal charges at the phase time point g to open the electronic shutter are accumulated in the floating diffusion layer 406.

As a consequence of causing the first light source 104 to perform the pulsed light emission in accordance with the irradiation pattern indicated with the circled number 2, the signal charges at the phase time point g to open the electronic shutter are accumulated in the floating diffusion layer 407.

Next, the second light sources 107 and 108 are subsequently operated likewise as shown in FIG. 14B. Hence, as a consequence of causing the second light source 107 to perform the pulsed light emission in accordance with the irradiation pattern indicated with the circled number 1, the signal charges at the phase time point f to open the electronic shutter are accumulated in the floating diffusion layer 408.

As a consequence of causing the second light source 108 to perform the pulsed light emission in accordance with the irradiation pattern indicated with the circled number 2, the signal charges at the phase time point f to open the electronic shutter are accumulated in the floating diffusion layer 409.

As a consequence of causing the second light source 107 to perform the pulsed light emission in accordance with the irradiation pattern indicated with the circled number 1, the signal charges at the phase time point g to open the electronic shutter are accumulated in the floating diffusion layer 410.

As a consequence of causing the second light source 108 to perform the pulsed light emission in accordance with the irradiation pattern indicated with the circled number 2, the signal charges at the phase time point g to open the electronic shutter are accumulated in the floating diffusion layer 411.

The series of the operations mentioned above are defined as one set, and multiple sets of the operations are repeated within one frame until the required signal charges are accumulated. The operations may be repeated for several tens of sets.

When one frame is regarded as the accumulation period of the signal charges, pseudo-synchronization of the irradiation with the first light sources 103 and 104 as well as the second light sources 107 and 108 can be achieved by repeating the operations as described above.

Next, operations to read the signal charges accumulated in the floating diffusion layers 404, 405, 406, 407, 408, 409, 410, and 411 are conducted by using the image sensor as with the Embodiment 1.

The operations to read the signals by using the image sensor are the same as those of the Embodiment 1, and description thereof will be omitted.

The Embodiment 2 has described the case where the light irradiation pattern is formed of two dot patterns. However, the number of irradiation patterns of the light sources may be increased as needed. As for the shape of each pattern, a ring-shaped or line-shaped pattern may be employed instead.

In this case, the number of the floating diffusion layers of the image sensor may be increased as needed.

Next, the first signal processing circuit 115 performs separation of the shallow part and the deep part by use of data for eight images outputted from the time-resolved image sensor 113. Each of the eight images corresponds to the signal charges which are accumulated in the corresponding one of the floating diffusion layers 404, 405, 406, 407, 408, 409, 410, and 411, and are acquired in accordance of the corresponding irradiation pattern using the two wavelengths. As for the separation method, there have been known the method of solving simultaneous equations by using light reception data on multiple SD (source—detector; light transmission—light reception) distances as described in JP 2012-125370 A, the subtraction method using an adaptive filter, and so forth.

Furthermore, it is possible to improve accuracy and reliability of a solution to be found by adding a difference method by means of normalization and further simultaneous equations based on a change in ratio between the shallow part and the deep part depending on the difference between the phase time points f and g to open the electronic shutter.

Here, as described above, more light components immediately after settlement of the surface reflection, and more light components internally scattered at the shallow part of the head are obtained at the phase time point f. On the other hand, more light components having passed through longer optical path lengths of the scattered light are detected at the phase time point g while reflecting further delays from the surface reflection. Due to a relative decrease in ratio of signal components originating at a shallow position, the ratio between the shallow part and the deep part may vary depending on the time point.

In the Embodiment 2, combinations of distances between all the pixels of the image sensor and light irradiation points in every dot pattern are made available as shown in FIG. 16 by using time-division light pattern irradiation and the time-resolved image sensor. Thus, it is possible to acquire numerous SD distance data.

Quadrille grids in FIG. 16 represent the pixel positions of the image sensor corresponding to the surface of the forehead of the subject, while circled numbers 1 and 2 represent positions of irradiation patterns with respective laser pulses. Arrows therein have the same meanings as those in FIG. 10.

It is possible to acquire the light irradiation dot patterns at two different positions, and the signals at steps each corresponding to a distance defined by (the length of the subject/the number of pixels of the image sensor). For example, in the case where the image sensor has 200 pixels in its horizontal direction and the subject has a horizontal length of 20 cm, then it is possible to acquire the signals of the SD distances of each dot pattern by the 1-mm step. This makes it possible to enhance accuracy to separate the shallow part and the deep part. Moreover, the use of the high speed time-resolved image sensor enables high speed image pickup in one frame.

After the first signal processing circuit 115 performs the separation of the shallow part and the deep part at 750 nm and 850 nm, respectively, the second signal processing circuit 116 computes relative changes in oxidized hemoglobin and deoxidized hemoglobin in each pixel from the images of the deep part separated at the two wavelengths while using the light absorption coefficients of oxidized hemoglobin and deoxidized hemoglobin at the respective wavelengths. Thus, it is possible to provide the brain activity imaging at high speed and high accuracy.

Here, depending on the subject to be measured, light absorption ratios of the two wavelengths mentioned above may be different from each other. In this case, if the absorption ratios are known in advance, then a time interval between the time point f and the time point g and a time interval between the time point f to a time point i may be changed for each of the light with the wavelength of 750 nm and the light with the wavelength of 850 nm.

The Embodiment 3

Next, Embodiment 3 of the present disclosure will be described. As compared to the image pickup apparatus 1002 of the Embodiment 2, an image pickup apparatus of the Embodiment 3 is different in that the apparatus includes a function to perform photoelectric conversion while dividing reflection light corresponding to one emitted pulse into two phases. In terms of hardware, the image pickup apparatus of the Embodiment 3 is the same as that of the Embodiment 2. Accordingly, reference is made to FIG. 12 in this example.

Different features from the Embodiment 2 will be mainly described below.

FIG. 13B is a diagram showing a light irradiation pattern of the Embodiment 3 of the present disclosure, which is the same as that in the Embodiment 2. Accordingly, description thereof will be omitted.

Detailed operations of the image pickup apparatus according to the Embodiment 3 of the present disclosure will be described below with reference to a timing chart of FIG. 17A, a timing chart of FIG. 17B, the schematic diagrams of FIGS. 1 and 12 showing the entire system, a timing charge of FIG. 18A, and a timing chart of FIG. 18B.

Figure 17A:
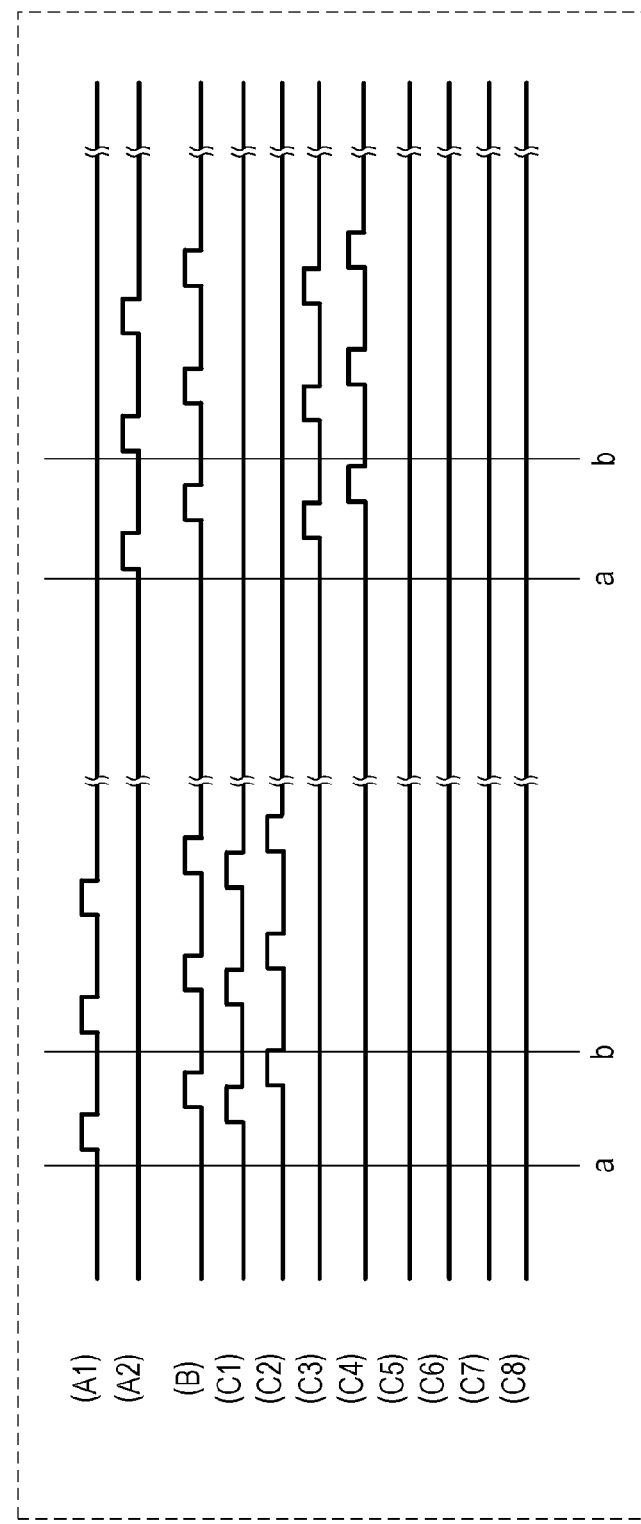
FIG. 17A is a timing chart showing operations of an image pickup apparatus of Embodiment 3.

In FIGS. 17A and 17B, signals A1, A2, A5, and A6 indicate light emission timings from the first light sources 103 and 104 as well as the second light sources 107 and 108, respectively. A signal B therein indicates timings to open and close the electronic shutter. Signals C1, C2, C3, C4, C5, C6, C7, and C8 indicate timings to turn the floating diffusion layers 404, 405, 406, 407, 408, 409, 410, and 411 on (i.e., the state where the electric charges are accumulated in the floating diffusion layers) and off (i.e., the state where the electric charges are not accumulated in the floating diffusion layers), respectively. Meanwhile, in FIGS. 18A and 18B, a signal A indicates a light emission timing of a light source, a signal B indicates timings to open and close the electronic shutter during a period from a time point a to a time point b, signals C1, C3, C5, C7 indicate timings to turn the floating diffusion layers 404, 406, 408, and 410 on and off, signals C2, C4, C6, C8 indicate timings to turn the floating diffusion layers 405, 407, 409, and 411 on and off, a signal D indicates an intensity of a surface-reflected light component reaching the time-resolved image sensor 113, a signal E indicates an intensity of an internally scattered light component reaching the time-resolved image sensor 113, and a signal F indicates a sum of the signal D and the signal E.

The control circuit 114 in FIGS. 1 and 12 causes the first light source 103 to emit light multiple times at a pulse width of about 10 ns and at a frequency of about 10 MHz as shown in FIG. 17A. The irradiation may usually be repeated about 1000 times in a period of about 100 µsec, for example.

Figure 18A:
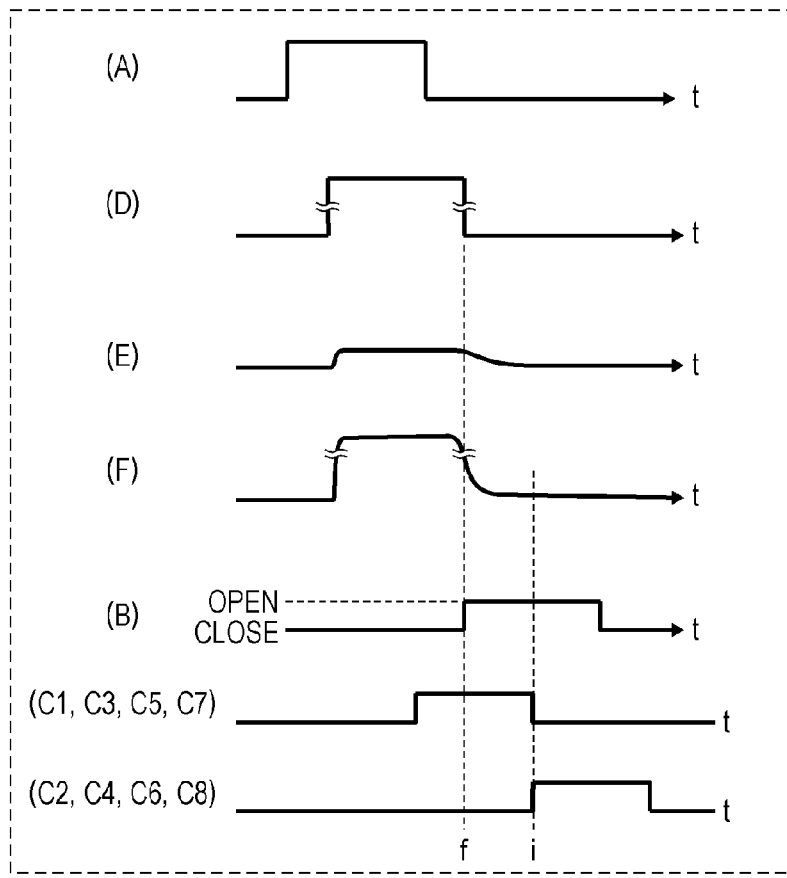
FIG. 18A is a timing chart showing detailed operations of the image pickup apparatus of the Embodiment 3.

As shown in FIG. 18A, as a consequence of release control of unnecessary electric charges to a drain conducted by the high speed timing control circuit 412 (FIG. 5), the time-resolved image sensor 113 performs control so as to close the electronic shutter during the period when the electric charges are released to the drain, and to open the electronic shutter during the period when the electric charges are not released to the drain.

Figure 18B:
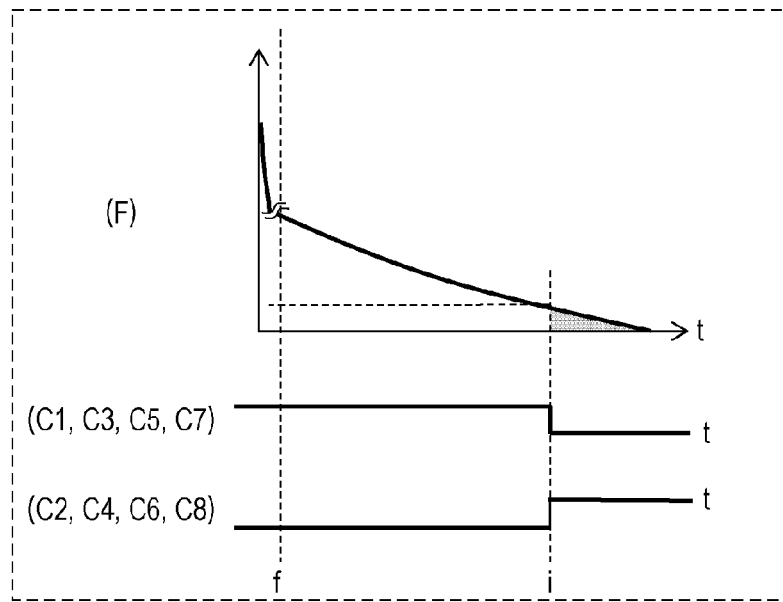
FIG. 18B is another timing chart showing detailed operations of the image pickup apparatus of the Embodiment 3.

Here, FIG. 18B is a timing chart showing an enlarged section around the time point f to the time point i in the timing chart of FIG. 18A. Based on an instruction from the control circuit 114, the high speed timing control circuit 412 sets a time point to start opening the electronic shutter at the time point f of disappearance of the surface-reflected light component. Moreover, the high speed timing control circuit 412 maintains the open period of the electronic shutter for a period corresponding to the width of the emitted light pulse, and closes the electronic shutter immediately thereafter.

At this time, the floating diffusion layer 404 has been activated by the high speed timing control circuit 412 when the electronic shutter is opened, and is turned off at the time point i in FIG. 18B in the middle of the period when the electronic shutter is opened. At the same time, the floating diffusion layer 405 is activated by the high speed timing control circuit 412 at the time point i. The diffusion layer 405 is kept active until the timing to close the electronic shutter, and is then turned off.

As the first light source 103 emits the pulsed light repeatedly, the electric shutter and the control of the floating diffusion layers 404 and 405 are also operated in response to the light emission from the first light source 103 as shown in FIG. 17A.

The signal charges in the first half (until the time point i) of an effective period of opening the electronic shutter are accumulated in the floating diffusion layer 404 while the signal charges in the last half (after the time point i) of the effective period of opening the electronic shutter are accumulated in the floating diffusion layer 405 by the control of the high speed timing control circuit 412. The rest of the diffusion layers are turned off during this period. Note that this device is designed such that all the electric charges in the photodetector are released to the drain when the release to the drain is active.

As with the Embodiment 2, the signal charge components in the floating diffusion layer 404 contain a sufficiently larger amount of the information on the shallow part than the information on the deep part. As a consequence, the signal charge components contain a sufficiently larger amount of scalp blood flow components than cerebral blood flow components.

On the other hand, as compared to the signal charge components acquired starting the time f, the signal charge components in the floating diffusion layer 405 contain a higher ratio of the information on the deep part, and a ratio of the cerebral blood flow components therein is increased as a consequence.

The above-mentioned ratio is changed by accumulating the signal charges in the floating diffusion layer 404 and the floating diffusion layer 405 while dividing the operation timings of the electronic shutter into the first half and the last half.

Next, the control circuit 114 in FIGS. 1 and 12 causes the first light source 104 to emit light multiple times at the pulse width of about 10 ns and at the frequency of about 10 MHz as shown in FIG. 17A.

As shown in FIG. 18A, as a consequence of the release control of unnecessary electric charges to the drain conducted by the high speed timing control circuit 412 (FIG. 5), the time-resolved image sensor 113 performs control so as to close the electronic shutter during the period when the electric charges are released to the drain, and to open the electronic shutter during the period when the electric charges are not released to the drain.

Based on an instruction from the control circuit 114, the high speed timing control circuit 412 sets a time point to start opening the electronic shutter at the time point f of disappearance of the surface-reflected light component. Moreover, the high speed timing control circuit 412 maintains the open period of the electronic shutter for a period corresponding to the width of the emitted light pulse, and closes the electronic shutter immediately thereafter.

The floating diffusion layer 406 has been activated by the high speed timing control circuit 412 when the electronic shutter is opened, and is turned off at the time point i in FIG. 18B in the middle of the period when the electronic shutter is opened. At the same time, the floating diffusion layer 407 is activated by the high speed timing control circuit 412 at the time point i. The diffusion layer 407 is kept active until the timing to close the electronic shutter, and is then turned off.

As the first light source 104 emits the pulsed light repeatedly, the electric shutter and the control of the floating diffusion layers 406 and 407 are also operated in response to the light emission from the first light source 104 as shown in FIG. 17A.

The signal charges in the first half (until the time point i) of the effective period of opening the electronic shutter are accumulated in the floating diffusion layer 406 while the signal charges in the last half (after the time point i) of the effective period of opening the electronic shutter are accumulated in the floating diffusion layer 407 by the control of the high speed timing control circuit 412. The rest of the diffusion layers are turned off during this period. Note that this device is designed such that all the electric charges in the photodetector are released to the drain when the release to the drain is active.

As a result of the above-described operations, the signal charges are independently accumulated as described below.

As a consequence of causing the first light source 103 to perform the pulsed light emission in accordance with the irradiation pattern indicated with the circled number 1, the signal charges until the time point i representing the first half of the period of opening the electronic shutter are accumulated in the floating diffusion layer 404 while the signal charges after the time point i representing the last half of the period of opening the electronic shutter are accumulated in the floating diffusion layer 405.

As a consequence of causing the first light source 104 to perform the pulsed light emission in accordance with the irradiation pattern indicated with the circled number 2, the signal charges until the time point i representing the first half of the period of opening the electronic shutter are accumulated in the floating diffusion layer 406 while the signal charges after the time point i representing the last half of the period of opening the electronic shutter are accumulated in the floating diffusion layer 407.

Next, as shown in FIG. 17B, the pulsed laser light sources 1 and 2 with the wavelength of 850 nm are subsequently operated in a similar manner. Thus, the signal charges are independently accumulated as described below.

As a consequence of causing the second light source 107 to perform the pulsed light emission in accordance with the irradiation pattern indicated with the circled number 1, the signal charges until the time point i representing the first half of the period of opening the electronic shutter are accumulated in the floating diffusion layer 408 while the signal charges after the time point i representing the last half of the period of opening the electronic shutter are accumulated in the floating diffusion layer 409.

As a consequence of causing the second light source 108 to perform the pulsed light emission in accordance with the irradiation pattern indicated with the circled number 2, the signal charges until the time point i representing the first half of the period of opening the electronic shutter are accumulated in the floating diffusion layer 410 while the signal charges after the time point i representing the last half of the period of opening the electronic shutter are accumulated in the floating diffusion layer 411.

The series of the operations mentioned above are defined as one set, and multiple sets of the operations are repeated within one frame until the required signal charges are accumulated. The operations may be repeated for several tens of sets.

Next, the first signal processing circuit 115 performs separation of the shallow part and the deep part by use of data for eight images outputted from the time-resolved image sensor 113, each of which corresponds to one of the floating diffusion layers 404, 405, 406, 407, 408, 409, 410, and 411, and is acquired in accordance of the corresponding irradiation pattern using the two wavelengths. As for the separation method, the same principle as that of the Embodiment 2 is basically applied, and description thereof will be omitted.

Since the signal charges of the two phases are detectable by the emission of one pulse, it is possible to provide an image pickup apparatus operable at a higher speed than the apparatus of the Embodiment 2.

Embodiment 4

Next, Embodiment 4 of the present disclosure will be described. An image pickup apparatus of the Embodiment 4 targets at a light-scattering body like a living body as its subject. Specifically, the image pickup apparatus detects density distribution conditions and temporal changes of oxidized hemoglobin and deoxidized hemoglobin in the brain to be observed, and constructs the density distribution conditions in the form of two-dimensional images.

While the objective of the Embodiment 4 is the same as the objective of the Embodiment 1, the Embodiment 4 is different from the Embodiment 1 in that the Embodiment 4 includes a single first light source 103 which emits the pulsed laser light with the wavelength of 750 nm, and a single second light source 107 which emits the pulsed laser light with the wavelength of 850 nm.

The following description will be given by mainly focusing on different features from the Embodiment 1. Structures and/or functions of constituents not particularly explained herein are the same as those of the configuration of the image pickup apparatus 1001 of the Embodiment 1.

Figure 19:
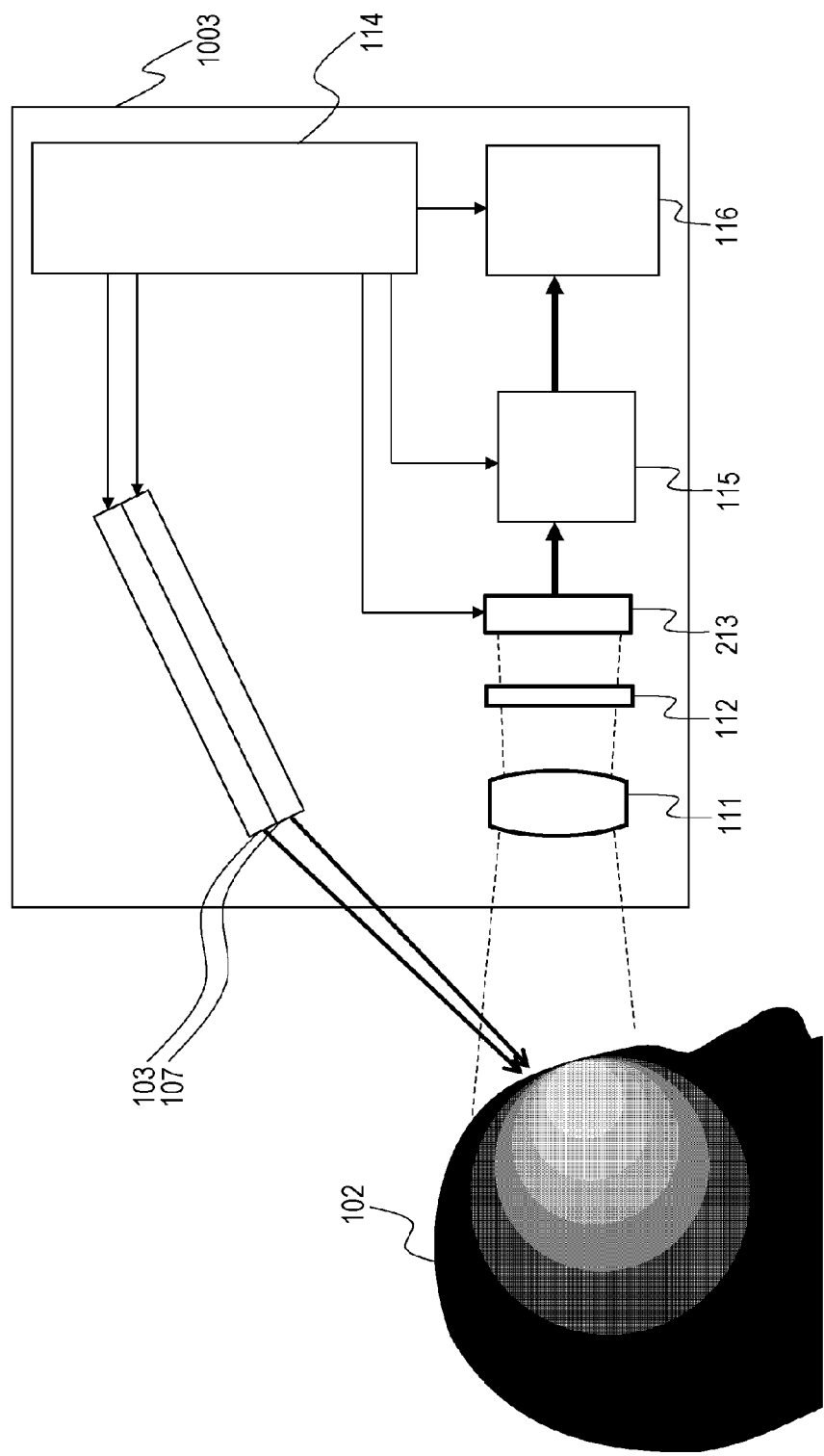
FIG. 19 is an image pickup system diagram including an image pickup apparatus of the Embodiment 4.

FIG. 19 is an image pickup system diagram including an image pickup apparatus 1003 of the Embodiment 4.

Different features of the image pickup apparatus 1003 from those of the image pickup apparatus 1001 of the Embodiment 1 include the number of light sources and a configuration and operations of a time-resolved image sensor 213. Due to these different features, operations of the control circuit 114 are also different. Nonetheless, these apparatuses are the same in terms of hardware except the configuration of the time-resolved image sensor 213. Accordingly, the same names and reference signs are employed herein. Operations of the image pickup apparatus 1003 inclusive of the operations of the control circuit 114 therein will be described below in detail.

The image pickup apparatus 1003 includes the single first light source 103 which emits pulsed laser light with the wavelength of 750 nm, and the single second light source 107 which emits pulsed laser light with the wavelength of 850 nm. Each light source performs irradiation at short pulses, high speed, and in a repeated manner in accordance with a predetermined pattern to be described later.

Figure 20B:
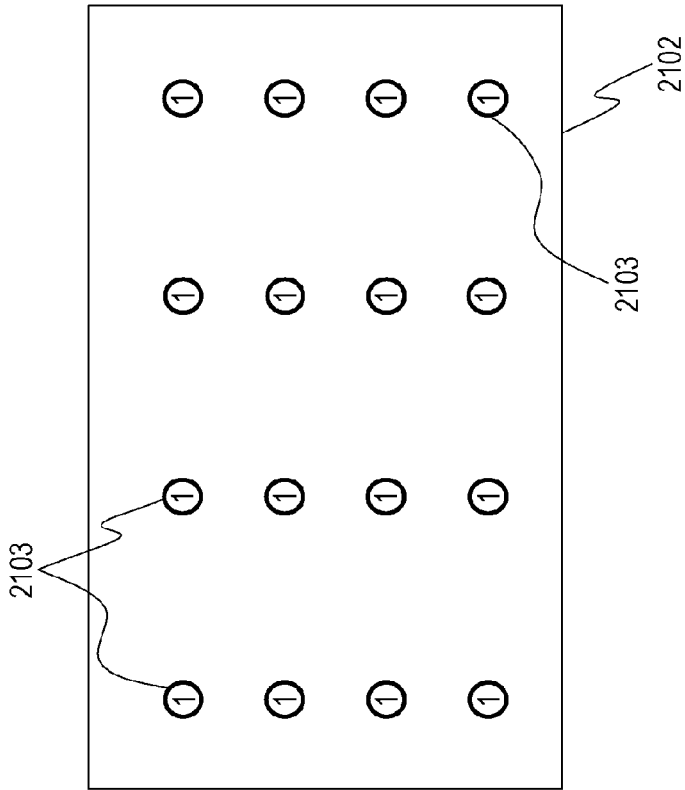
FIG. 20B is a diagram showing an example of a light irradiation pattern to be emitted to the head (the forehead)
Figure 20A:
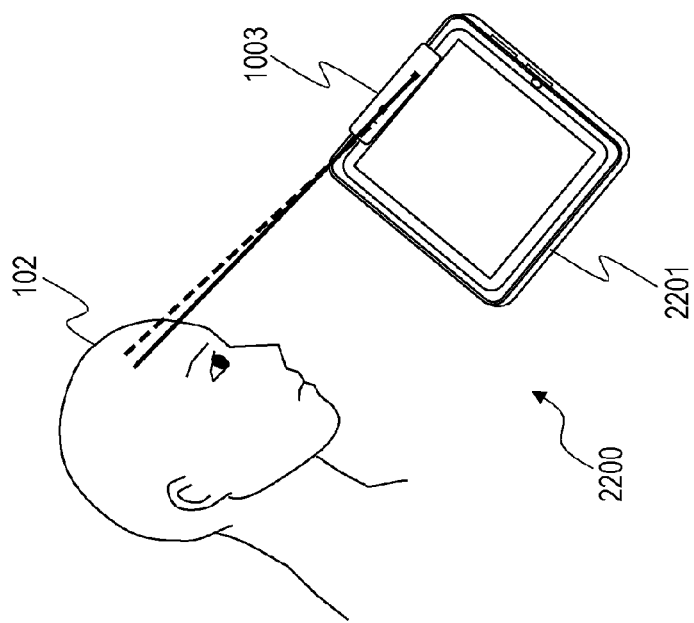
FIG. 20A is a diagram showing a usage scene of the image pickup apparatus of the Embodiment 4.

FIG. 20A shows a usage scene 2200 of the image pickup apparatus 1003 of the Embodiment 4. The image pickup apparatus 1003 is built in a tablet terminal 2201. For example, the image pickup apparatus 1003 emits first and second irradiation light beams at different time points 1 and 2, respectively. Firstly, light beams with the wavelength of 750 nm are emitted as the first and second irradiation light beams from the first light source 103. When the light emission is completed, light beams with the wavelength of 850 nm are subsequently emitted from the second light sources 107. Locations of the respective irradiation light beams are determined in advance such that the respective irradiation light beams are made incident on particular positions of the head 102. In other words, each light irradiation pattern representing a pattern of an image formed by the irradiation is determined in advance.

FIG. 20B shows an example of a light irradiation pattern 2102 to be emitted to the head 102.

Positions 2103 indicated with the circled number 1 in FIG. 20B represent positions of light dot patterns formed by the laser beams emitted from the first light source 103 and the second light source 107, respectively. The first light source 103 and the second light source 107 perform the irradiation in a time-division manner at different time points in one frame at operation timings to be described later. In the Embodiment 4, the positions of the light dot pattern formed by the laser beams emitted from the first light source 103 are identical to the positions of the light dot pattern formed by the laser beams emitted from the second light source 107.

In the Embodiment 4, the characteristics of the optical double band pass filter 112 are the same as those illustrated in FIG. 4. Accordingly, duplicate explanations thereof will be omitted.

Figure 21:
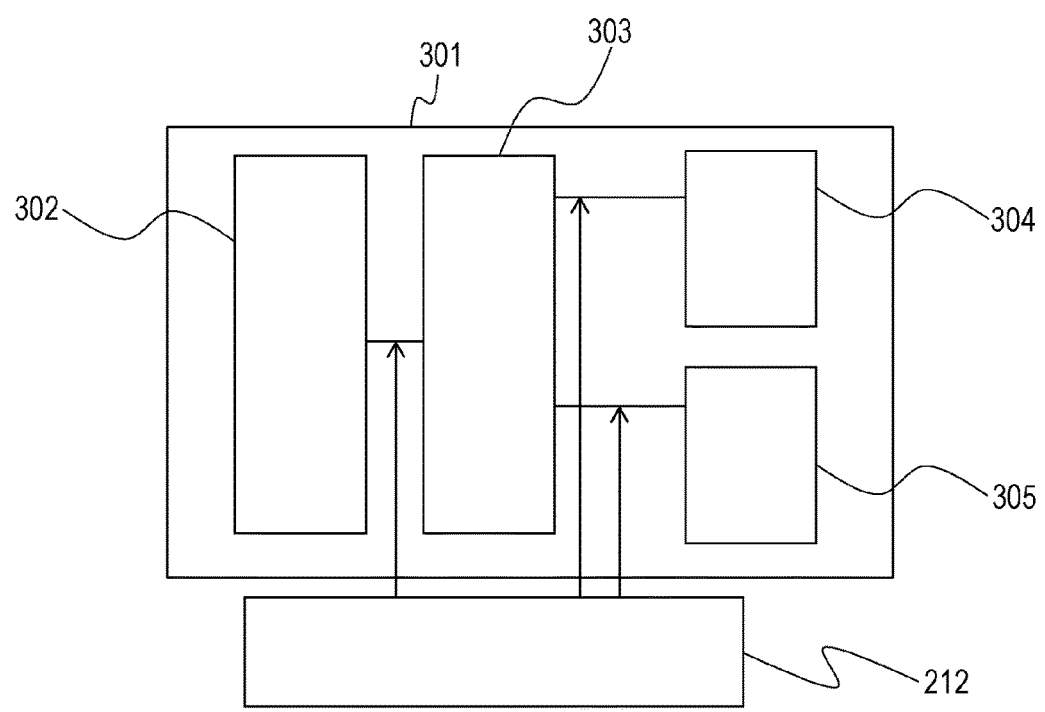
FIG. 21 is a configuration diagram of one pixel in a time-resolved image sensor.

A configuration of each pixel of the time-resolved image sensor 213 of the Embodiment 4 shown in FIG. 21 is different from that of the Embodiment 1. Accordingly, a description will be given of this point.

FIG. 21 is a configuration diagram of one pixel 301 in the time-resolved image sensor 213. The one pixel 301 includes: a drain 302 which is a charge release part; a photodetector (PD) 303 which is a photoelectric converter; two floating diffusion layers (FD) 304 and 305 which are accumulators to accumulate signal charges; and a high speed timing control circuit 212.

The photodetector 303 converts incident photons into signal electrons (signal charges). The high speed timing control circuit 212 outputs control signals and switches whether each signal charge is to be released to the drain 302 or to be accumulated in any one of the floating diffusion layers 304 and 305. The way to determine to which one of the floating diffusion layers 304 and 305 the signal charge is to be accumulated depends on timings to be described later. An operating speed required by these timings is in the order of nanoseconds. To achieve the high speed operations, the high speed timing control circuit 212 is formed of a CMOS logic circuit, for example.

The configuration of the time-resolved image sensor 213 of the Embodiment 4 is different from that of the time-resolved image sensor 113 of the Embodiment 1 in that the time-resolved image sensor 213 includes the two floating diffusion layers 304 and 305 in one pixel region. In this way, electric charges accumulated in one pixel region are treated as if they are signals representing two pixels (either in one row and two columns or in two rows and one column) of a general CMOS image sensor, and are thus outputted from the time-resolved image sensor 213.

Detailed operations of the image pickup apparatus according to the Embodiment 4 of the present disclosure will be described below with reference to the system configuration diagram of FIG. 19.

The control circuit 114 in FIG. 19 causes the first light source 103 to emit light multiple times at a pulse width of about 10 ns and at a frequency of about 10 MHz as shown in FIG. 7A, for example. The irradiation is usually repeated about 1000 times in a period of about 100 μsec, for instance. In this case, the irradiation dot pattern is formed at the positions on the forehead indicated with the circled number 1 in FIG. 20B. For example, intervals between the positions indicated with the circled number 1 are set to about 3 cm in horizontal and vertical directions, and to 4.24 cm in a diagonal direction calculated by multiplying each interval by the "square root of 2".

Behaviors of the light components of the respective wavelengths incident on the forehead, and the principle of detection of the internally scattered light components are the same as those of the Embodiment 1. The degrees of the attenuation of the internally scattered light components are the same as well.

In the meantime, regarding the operations of the first light source 103 and the second light source 107, these light sources may be conducted as in the case of any of the Embodiments 1, 2, and 3. Moreover, the operations to open and/or close the electronic shutter corresponding thereto as well as the operations to turn on and/or off the floating diffusion layers 304 and 305 in response to the operations of the light sources may also be conducted likewise. Accordingly, description of these operations will be omitted.

Next, a description will be given of accumulation of the signal charges in the Embodiment 4.

As a consequence of causing the first light source 103 to perform the pulsed light emission in accordance with the irradiation pattern indicated with the circled number 1 in FIG. 20B, the signal charges at the phase time point f or g to open the electronic shutter in FIG. 15A are accumulated in the floating diffusion layer 304.

Meanwhile, as a consequence of causing the second light source 107 to perform the pulsed light emission in accordance with the irradiation pattern indicated with the circled number 1 in FIG. 20B, the signal charges at the phase time point f or g to open the electronic shutter in FIG. 15A are accumulated in the floating diffusion layer 305.

In this case, the same phase time point to open the electric shutter is preferably applied to both the signal charges to be accumulated in the floating diffusion layer 304 and the signal charges to be accumulated in the floating diffusion layer 305.

The series of the operations mentioned above are defined as one set, and multiple sets of the operations are repeated within one frame until the required signal charges are accumulated. The operations may be repeated for several tens of sets.

When one frame is regarded as the accumulation period of the signal charges, pseudo-synchronization of the irradiation with the first light source 103 and the second light source 107 can be achieved by repeating the operations as described above.

Next, operations to read the signal charges accumulated in the floating diffusion layers 304 and 305 are conducted by using the image sensor as with the Embodiment 1.

The operations to read the signals by using the image sensor are the same as those of the Embodiment 1, and description thereof will be omitted.

The Embodiment 4 has described the case where the light irradiation pattern is formed of one dot pattern. However, the number of irradiation patterns of the light sources may be increased as needed. As for the shape of each pattern, a ring-shaped or line-shaped pattern may be employed instead.

In this case, the number of the floating diffusion layers of the image sensor may be increased as needed.

Next, the first signal processing circuit 115 performs separation of the shallow part and the deep part by use of data for two images outputted from the time-resolved image sensor 213. Each of the two images corresponds to the signal charges which are accumulated in the corresponding one of the floating diffusion layers 304 and 305, and are acquired in accordance of the corresponding irradiation pattern using the two wavelengths. As for the separation method, there have been known the method of solving simultaneous equations by using light reception data on multiple SD (source—detector; light transmission—light reception) distances as described in JP 2012-125370 A, the subtraction method using an adaptive filter, and so forth.

Here, as described above, more light components immediately after settlement of the surface reflection, and more light components internally scattered at the shallow part of the head are obtained at the phase time point f. On the other hand, more light components having passed through longer optical path lengths of the scattered light are detected at the phase time point g while reflecting further delays from the surface reflection. Due to a relative decrease in ratio of signal components originating at a shallow position, the ratio between the shallow part and the deep part may vary with the time point.

After the first signal processing circuit 115 performs the separation of the shallow part and the deep part at 750 nm and 850 nm, respectively, the second signal processing circuit 116 computes relative changes in oxidized hemoglobin and deoxidized hemoglobin in each pixel from the images of the deep part separated at the two wavelengths while using the light absorption coefficients of oxidized hemoglobin and deoxidized hemoglobin at the respective wavelengths. Thus, it is possible to provide the brain activity imaging at high speed and high accuracy.

The examples of the Embodiment of the present disclosure have been described above.

According to each Embodiment described above, the image pickup apparatus includes the image sensor having the floating diffusion layers, each of which serves as the accumulator to independently accumulate the signal charges for the corresponding pixel. The image sensor is provided with the electronic shutter function. The irradiation light pattern is emitted from each pulsed light source while changing the positions in a time-division manner within one frame. Then, the signals for the respective irradiation patterns are repeatedly accumulated in the accumulators by using the high speed electronic shutter function every time the pulsed light irradiation takes place. As a consequence, it is possible to achieve separation by computation of the shallow part and the deep part of the subject at high accuracy, and thus to remove artifacts attributed to the scalp blood flow at high speed and high accuracy in the course of cerebral blood flow imaging, which has previously been considered to be difficult, for example.

The above-described Embodiments explain the case of using the light sources with two wavelengths. However, the present disclosure is also applicable to an image pickup apparatus which performs image pickup by using a light source with one wavelength.

Furthermore, although the time-resolved image sensor 113 provided with the eight floating diffusion layers has been explained in certain Embodiments, this configuration is just one example. The time-resolved image sensor at least needs two floating diffusion layers. If the time-resolved image sensor can repeatedly accumulate the signal charges by using the high speed shutter function every time the pulsed light irradiation takes place and for each of the irradiation patterns within one frame, then the number of the floating diffusion layers may be two, or more than two.

Although the above-described Embodiments have discussed the case of applying the image pickup apparatus of the aspects of the present disclosure to bioinstrumentation. However, the present disclosure is not limited to this configuration. The image pickup apparatus of the aspects of the present disclosure may also be applied, for example, to a picking robot and the like. Furthermore, the image pickup apparatus may also be applicable, for example, to a material analyzer, a food analyzer, and the like.

Meanwhile, the above-described Embodiments have discussed the case in which each light source emits one light irradiation pattern. However, the present disclosure is not limited to this configuration. Each light source may be enabled to emit two or more light irradiation patterns by switching the light irradiation patterns to be emitted therefrom.

What is claimed is:

1. An image pickup apparatus comprising:
   a first light source which, in operation, emits a first pulsed light beam to project a first image of a first pattern at a first position in a predetermined region of a subject, and emits a second pulsed light beam to project a second image of a second pattern at a second position in the predetermined region of the subject, the second position being different from the first position;
   an image sensor including pixels, each of the pixels including:
      a photodetector which, in operation, converts received light into a signal charge, and
      a first accumulator and a second accumulator each of which, in operation, accumulates the signal charge at a different timing; and
   a control circuit which, in operation, controls the first light source and the image sensor, wherein:
   the first pulsed light beam does not irradiate at least a part of the second position,
   the second pulsed light beam does not irradiate at least a part of the first position, the control circuit, in operation:
> causes the first light source to emit the first pulsed light beam,
> causes the first accumulator to accumulate a first signal charge generated in the photodetector by a first return light corresponding to the first pulsed light beam,
> causes the first light source to emit the second pulsed light beam at a different time point from a time point of the emission of the first pulsed light beam, and
> causes the second accumulator to accumulate a second signal charge generated in the photodetector by a second return light corresponding to the second pulsed light beam.

2. The image pickup apparatus according to claim 1, further comprising:
a signal processing circuit which, in operation, generates image information by using the first signal charge and the second signal charge.

3. The image pickup apparatus according to claim 1, wherein each of the first pattern and the second pattern is a pattern including dots.

4. The image pickup apparatus according to claim 1, wherein each of the first pattern and the second pattern is a pattern including rings.

5. The image pickup apparatus according to claim 1, wherein each of the first pattern and the second pattern is a pattern including lines.

6. The image pickup apparatus according to claim 1, wherein, in operation,
the control circuit causes the first light source to emit a plurality of first pulsed light beams, each of the plurality of first pulsed light beams being the first pulsed light beam, and
the control circuit causes the first light source to emit a plurality of second pulsed light beams, each of the plurality of second pulsed light beams being the second pulsed light beam.

7. The image pickup apparatus according to claim 1, further comprising:
a second light source which, in operation, emits a third pulsed light beam to project a third image of a third pattern at a third position in the predetermined region of the subject, the third position being different from the first and second positions, and emits a fourth pulsed light beam to project a fourth image of a fourth pattern at a fourth position in the predetermined region of the subject, the fourth position being different from the first, second, and third positions, wherein:
each of the pixels further includes a third accumulator and a fourth accumulator each of which, in operation, accumulates the signal charge,
the first pulsed light beam and the second pulsed light beam are in a first wavelength range,
the third pulsed light beam and the fourth pulsed light beam are in a second wavelength range different from the first wavelength range,
the control circuit, in operation, further controls the second light source, and
the control circuit, in operation:
> causes the second light source to emit the third pulsed light beam,
> causes the third accumulator to accumulate a third signal charge generated in the photodetector by a third return light corresponding to the third pulsed light beam,
> causes the second light source to emit the fourth pulsed light beam at a different time point from a time point of the emission of the third pulsed light beam, and
> causes the fourth accumulator to accumulate a fourth signal charge generated in the photodetector by a fourth return light corresponding to the fourth pulsed light beam.

8. The image pickup apparatus according to claim 7, further comprising:
a signal processing circuit which, in operation, generates image information by using the first to fourth signal charges.

9. The image pickup apparatus according to claim 1, wherein:
each of the pixels further includes a third accumulator and a fourth accumulator each of which, in operation, accumulates the signal charge, and
the control circuit, in operation:
> causes the first light source to emit the first pulsed light beam at a first time point and at a second time point,
> causes the first accumulator to accumulate the first signal charge after a lapse of a first time period from the first time point,
> causes the third accumulator to accumulate the first signal charge after a lapse of a second time period from the second time point, the second time period being longer than the first time period,
> causes the first light source to emit the second pulsed light beam at a third time point and at a fourth time point,
> causes the second accumulator to accumulate the second signal charge after a lapse of a third time period from the third time point, and
> causes the fourth accumulator to accumulate the second signal charge after a lapse of a fourth time period from the fourth time point, the fourth time period being longer than the third time period.

10. The image pickup apparatus according to claim 1, wherein each of the first pulsed light beam and the second pulsed light beam is a near infrared light beam.

11. An image pickup apparatus comprising:
a light source which, in operation, emits a first pulsed light beam to project a first image of a first pattern at a first position in a predetermined region of a subject, and emits a second pulsed light beam to project a second image of a second pattern at a second position in the predetermined region of the subject, the second position being different from the first position;
an image sensor including pixels, each of the pixels including
> a photodetector which, in operation, converts received light into a signal charge, and
> a first accumulator and a second accumulator each of which, in operation, accumulates the signal charge; and
a control circuit which, in operation, controls the light source and the image sensor, wherein:
the first pulsed light beam does not irradiate at least a part of the second position,
the second pulsed light beam does not irradiate at least a part of the first position,
the control circuit, in operation,
> causes the light source to emit the first pulsed light beam at a first time point,
> causes the first accumulator to accumulate the signal charge in a period after the first time point until a second time point, causes the second accumulator to accumulate the signal charge after the second time point, causes the light source to emit the second pulsed light beam at a third time point, causes the first accumulator to accumulate the signal charge in a period after the third time point until a fourth time point, and causes the second accumulator to accumulate the signal charge after the fourth time point.

12. The image pickup apparatus according to claim 11, wherein each of the first pulsed light beam and the second pulsed light beam is a near infrared light beam.

13. An image pickup apparatus comprising:

a first light source which, in operation, emits a first pulsed light beam to project a first image of a first pattern at a first position in a predetermined region of a subject, and emits a second pulsed light beam to project a second image of a second pattern at a second position in the predetermined region of the subject, the second position being different from the first position;

an image sensor including pixels, each of the pixels including:

a photodetector which, in operation, converts received light into a signal charge, and a first accumulator and a second accumulator each of which, in operation, accumulates the signal charge at a different timing; and a control circuit which, in operation, controls the first light source and the image sensor, wherein:

the control circuit, in operation:

causes the first light source to emit the first pulsed light beam, causes the first accumulator to accumulate a first signal charge generated in the photodetector by a first return light corresponding to the first pulsed light beam, causes the first light source to emit the second pulsed light beam at a different time point from a time point of the emission of the first pulsed light beam, and causes the second accumulator to accumulate a second signal charge generated in the photodetector by a second return light corresponding to the second pulsed light beam, the subject is a light-scattering body, the first signal charge is an internally scattered light component originating from the first pulsed light beam and arriving from the subject, and the second signal charge is an internally scattered light component originating from the second pulsed light beam and arriving from the subject.

* * * * *